US006183951B1

(12) United States Patent
Plevy et al.

(10) Patent No.: US 6,183,951 B1
(45) Date of Patent: Feb. 6, 2001

(54) METHODS OF DIAGNOSING CLINICAL SUBTYPES OF CROHN'S DISEASE WITH CHARACTERISTIC RESPONSIVENESS TO ANTI-TH1 CYTOKINE THERAPY

(75) Inventors: Scott E. Plevy, Tenafly, NJ (US); Stephan R. Targan, Santa Monica, CA (US); Kent Taylor, Santa Paula, CA (US); Mary J. Barry, Ramona, CA (US)

(73) Assignee: Prometheus Laboratories, Inc., San Diego, CA (US)

( * ) Notice: Under 35 U.S.C. 154(b), the term of this patent shall be extended for 0 days.

(21) Appl. No.: 08/855,825

(22) Filed: May 12, 1997

Related U.S. Application Data

(63) Continuation-in-part of application No. 08/837,056, filed on Apr. 11, 1997, now abandoned.

(51) Int. Cl.[7] ....................................................... C12Q 1/68
(52) U.S. Cl. ........................... 435/6; 435/7.1; 424/184.1; 424/85.1; 536/24.3; 536/24.33
(58) Field of Search ........................ 435/7.1, 6; 536/24.3, 536/24.33; 424/184.1, 85.1

(56) References Cited

FOREIGN PATENT DOCUMENTS

WO 95/31575  11/1995  (WO).
WO 96/12189  4/1996  (WO).

OTHER PUBLICATIONS

Broekroelofs et al., "Anti–Neutrophil Cytoplasmic Antibodies (ANCA) in Sera from Patients with Inflammatory Bowel Disease (IBD)," *Dig. Dis. Sci.* 39:545–549 (1994).
Cambridge et al., "Anti–neutrophil Antibodies in Inflammatory Bowel Disease: Prevalence and Diagnostic Role," *Gut* 33:668–674 (1992).
Crouau–Roy et al., "Tumor Necrosis Factor Microsatellites in Four European Populations," *Human Immunol.* 38:213–216 (1993).
Duerr et al., "Anti–neutrophil Cytoplasmic Antibodies in Ulcerative Colitis," *Gastroenterol.*, 100:1590–1596 (1991).
Fuss et al., "Disparate CD4+ Lamina Propria (LP) Lymphokine Secretion Profiles in Inflammatory Bowel Disease," *J. Immunol.* 157:1261–1270 (1996).
Hanauer, "Inflammatory Bowel Disease," *New Engl. J. Med.* 334:841–848 (1996).
Hardarson et al., "Antineutrophil Cytoplasmic Antibody in Inflammatory Bowel and Hepatobiliary Diseases," *Amer. J. Clin. Pathol.*99:277–281 (1993).
Jongeneel et al., "Extensive Genetic Polymorphism in the Human Tumor Necrosis Factor Region and Relation to Extended HLA Haplotypes," *Proc. Natl. Acad. Sci. USA*88:9717–9721 (1991).
Lennard–Jones, "Classification of Inflammatory Bowel Disease," *Scand. J. Gastroenterol. Suppl.* 24:2–6, 16–19 (1989).

MacDonald et al., "Tumor Necrosis Factor–Alpha and Interferon–Gamma Production Measured at the Single Cell Level in Normal and Inflamed Human Intestine," *Clin. Exp. Immunol.* 81:301–305 (1990).
Messer et al., "Polymorphic Structure of the Tumor Necrosis Factor (TNF) Locus: An NcoI Polymorphism in the First Intron of the Human TNF–β Gene Correlates With a Variant Amino Acid in Position 26 and a Reduced Level of TNF–β Production," *J. Exp. Med.* 173:209–219 (1991).
Mossman and Coffman, "TH1 and TH2 Cells: Different Patterns of Lymphokine Secretion Lead to Different Functional Properties," *Ann. Rev. Immunol.* 7:145–173 (1989).
Mullin et al., "Increased Interleukin–2 Messenger RNA in the Intestinal Mucosal Lesions of Crohn's Disease But Not Ulcerative Colitis," *Gastroenterology* 102:1620–1627 (1992).
Murch et al., "Location of Tumour Necrosis Factor α by Immunogistochemistry in Chronic Inflammatory Bowel Disease," *Gut* 34:1705–1709 (1993).
Nedospasov et al., "DNA Sequence Polymorphism at the Human Tumor Necrosis Factor (TNF) Locus," *J. Immunology* 147:1053–1059 (1991).
Orholm et al., "Familial Occurrence of Inflammatory Bowel Disease," *N. Engl. J. Med.,* 324:84–88 (1991).
Patel et al., "Influence of Total Colectomy on Serum Antineutrophil Cytoplasmic Antibodies in Inflammatory Bowel Disease," *Brit. J. Surg.* 81:724–726 (1994).
Pirmez et al., "Cytokine Patterns in the Pathogenesis of Human Leishmaniasis," *J. Clin. Invest.* 91:1390–1395 (1993).
Plevy and Targan, *Inflammatory Bowel Disease: From Bench to Bedside* Williams and Wilkens 582–609 (1993).
Plevy et al., "Increased Mucosal TNF–α mRNA Levels and Numbers of TNF–α Producing Cells are Unique to Crohn's Disease Mucosal Inflammation," *Gastroenterology* 106:A754 (1994).

(List continued on next page.)

*Primary Examiner*—Paula K. Hutzell
*Assistant Examiner*—Eliane Lazar-Wesley
(74) *Attorney, Agent, or Firm*—Campbell & Flores, LLP

(57) ABSTRACT

The present invention provides methods based on serological and genetic markers for diagnosing clinical subtypes of Crohn's disease (CD) having characteristic responsiveness to anti-Th1 cytokine therapy. In the methods of the inventions the presence of perinuclear anti-neutrophil antibody (pANCA), the presence of the TNFa10b4c1d3e3 haplotype or the presence TNFa11b4c1d3e3 haplotype each are independently diagnostic of a clinical subtype of CD having an inferior clinical response to anti-Th1 cytokine therapy. In addition, the presence of the homozygous TNF-β 1111 haplotype involving the TNFc, aa13L, aa26 and NcoI loci is independently diagnostic of a clinical subtype of CD having an inferior clinical response to anti-Th1 cytokine therapy. The presence of speckling anti-pan polymorphonuclear antibody (SAPPA) is diagnostic of a clinical subtype of CD having a superior clinical response to anti-Th1 cytokine therapy.

37 Claims, 10 Drawing Sheets

OTHER PUBLICATIONS

Plevy et al., "TNF–α mRNA Levels Differentiate Mucosal Inflammation in Crohn's Disease from Ulcerative Colitis," *J. Immunol.* 150:10A, abstract 41 (1993).

Plevy et al., "Tumor Necrosis Factor Microsatellites Define a Crohn's Disease–Associated Haplotype on Chromosome 6," *Gastroenterology* 110:1053–1060 (1996).

Pociot et al., "Association of Tumor Necrosis Factor (TNF) and Class II Major Histocompatibility Complex Alleles with the Secretion of TNF–α and TNF–β by Human Mononuclear Cells: A Possible Link to Insulin–Dependent Diabetes Mellitus," *Eur. J. Immunol.* 23:224–231 (1993).

Pool et al., "Serum Antineutrophil Cytoplasmic Autoantibodies in Inflammatory Bowel Disease are Mainly Associated with Ulcerative Colitis. A Correlation Study Between Between Perinuclear Antineutrophil Cytoplasmic Autoantibodies and Clinical Parameters, Medical, and Surgical Treatment," *Gut* 34:46–50 (1993).

Powrie et al., "Inhibition of Th1 Responses Prevents Inflammatory Bowel disease in scid Mice Reconsituted with CD45RB$^{hi}$ CD4$^+$ T Cells," *Immunity* 1:553–562 (1994).

Price, "Overlap in the Spectrum of Non–Specific Inflammatory Bowel Disease–'Colitis Indeterminate,'" *J. Clin. Pathol.* 31:567–577 (1978).

Proujansky et al., "Examination of Anti–neutrophil Cytoplasmic Antibodies in Childhood Inflammatory Bowel Disease," *J. Pediatr. Gastroenterol. Nutr.* 17:193–197 (1993).

Rubin and Farber (eds.), "Inflammatory Bowel Disease," *Pathology* (2nd Ed.), pp. 675–683 (1994).

Saxon et al., "A Distinct Subset of Antineutrophil Cytoplasmic Antibodies is Associated with Inflammatory Bowel Disease," *J. Allergy Clin. Immunol.* 86:202–210 (1990).

Schachter and Kirsner, "Difinitions of Inflammatory Bowel Disease of Unknown Etiology," *Gastroenterol.* 68:591–600 (1975).

Sung et al., "Anti–Neutrophil Cytoplasmic Antibodies (ANCA) and Inflammatory Bowel Diseases in Chinese," *Dig. Dis. Sci.* 39:886–892 (1994).

Targan and Murphy, "Clarifying the Causes of Crohn's," *Nature Med.* 1:1241–1243 (1995).

Udalova et al., "Highly Informative Typing of the Human TNF Locus Using Six Adjacent Polymorphic Markers," *Genomics* 16:180–186 (1993).

Van Dullemen et al., "Treatment of Crohn's Disease with Anti–Tumor Necrosis Factor Chimeric Monoclonal Antibody (cA2)," *Gastroenterol* 109:129–135 (1995).

Webb and Chaplin, "Genetic Variability at the Human Tumor Necrosis Factor Loci," *J. Immunol.* 145:1278–1285 (1990).

Vasiliauskas et al., "Perinuclear Antineutrophil Cytoplasmic Antibodies (pANCA) in Patients with Crohn's Disease (CD) Define a Clinical Subgroup," *Gastroenterol.* 108:A935 (1995).

Vasiliauskas et al., "Perinuclear Antineutrophil Cytoplasmic Antibodies in Patients with Crohn's Disease Define a Clinical Subgroup," *Gastroenterol.* 110:1810–19 (1996).

Plevy et al., "Tumor Necrosis Factor (TNF) Microsatellite Associations Within HLA–DR2+ Patients Define Crohn's Disease (CD) and Ulcerative Colitis (UC) Specific Genotypes," *Gastroenterology* 106:A754 (1994).

```
          10                      30                      50
           .           .           .           .           .           .
GGGGCTCCGCACAGCAGGTGAGGCTCTCCTGCCCCATCTCCTTGGGCTGCCCGTGCTTCG 70                      90                     110
           .           .           .           .           .           .
TGCTTTGGACTACCGCCCAGCAGTGTCCTGCCCTCTGCCTGGGCCTCGGTCCCTCCTGCA 130                     150                     170
           .           .           .           .           .           .
                                                        LEADER PEPTIDE
CCTGCTGCCTGGATCCCCGGCCTGCCTGGGCCTGGGCCTTGGTTCTCCCCATGACACCAC
                                                        MetThrProP 190                     210                     230
           .           .       Arg .           .           .
                                 C
CTGAACGTCTCTTCCTCCCAAGGGTGTGTGGCACCACCCTACACCTCCTCCTTCTGGGGC
roGluArgLeuPheLeuProArgValCysGlyThrThrLeuHisLeuLeuLeuLeuGlyL 250                     270                     290
           .           .           .           .           .           .
                                              ┌──► MATURE PROTEIN
TGCTGCTGGTTCTGCTGCCTGGGGCCCAGGGGCTCCCTGGTGTTGGCCTCACACCTTCAG
euLeuLeuValLeuLeuProGlyAlaGlnGly│LeuProGlyValGlyLeuThrProSerA 310                     330                     350
           .           .           .           .           .           .
CTGCCCAGACTGCCCGTCAGCACCCCAAGATGCATCTTGCCCACAGCACCCTCAAACCTG
LaAlaGlnThrAlaArgGlnHisProLysMetHisLeuAlaHisSerThrLeuLysProA 370                     390                     410
           .           .           .           .           .           .
CTGCTCACCTCATTGGAGACCCCAGCAAGCAGAACTCACTGCTCTGGAGAGCAAACACGG
LaAlaHisLeuIleGlyAspProSerLysGlnAsnSerLeuLeuTrpArgAlaAsnThrA
```

FIG. 4B

```
                430                     450                     470
                 .           .           .           .           .           .
ACCGTGCCTTCCTCCAGGATGGTTTCTCCTTGAGCAACAATTCTCTCCTGGTCCCCACCA
spArgAlaPheLeuGlnAspGlyPheSerLeuSerAsnAsnSerLeuLeuValProThrS 490                     510                     530
                 .           .           .           .           .           .
GTGGCATCTACTTCGTCTACTCCCAGGTGGTCTTCTCTGGGAAAGCCTACTCTCCCAAGG
erGlyIleTyrPheValTyrSerGlnValValPheSerGlyLysAlaTyrSerProLysA 550                     570                     590
                 .           .           .           .           .           .
CCACCTCCTCCCCACTCTACCTGGCCCATGAGGTCCAGCTCTTCTCCTCCCAGTACCCCT
laThrSerSerProLeuTyrLeuAlaHisGluValGlnLeuPheSerSerGlnTyrProP 610                     630                     650
                 .           .           .           .           .           .
TCCATGTGCCTCTCCTCAGCTCCCAGAAGATGGTGTATCCAGGGCTGCAGGAACCCTGGC
heHisValProLeuLeuSerSerGlnLysMetValTyrProGlyLeuGlnGluProTrpL 670                     690                     710
                 .           .           .           .           .           .
TGCACTCGATGTACCACGGGGCTGCGTTCCAGCTCACCCAGGGAGACCAGCTATCCACCC
euHisSerMetTyrHisGlyAlaAlaPheGlnLeuThrGlnGlyAspGlnLeuSerThrH 730                     750                     770
                 .           .           .           .           .           .
ACACAGATGGCATCCCCCACCTAGTCCTCAGCCCTAGTACTGTCTTCTTTGGAGCCTTCG
IsThrAspGlyIleProHisLeuValLeuSerProSerThrValPhePheGlyAlaPheA
```

FIG. 4C

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:1:

GCACTCCAGC CTAGGCCACA GA      22

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:2:

GCCTCTAGAT TTCATCCAGC CACA                                                          24

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:3:

CCTCTCTCCC CTGCAACACA CA                                                           22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

GTGTGTGTTG CAGGGGAGAG AG                                                           22

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:5:

GGTTTCTCTG ACTGCATCTT GTCC                                                       24

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

TCATGGGGAG AACCTGCAGA GAA                                                       23

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

AGATCCTTCC CTGTGAGTTC TGCT                                                      24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

```
CATAGTGGGA CTCTGTCTCC AAAG                                            24
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:9:

```
GTGCCTGGTT CTGGAGCCTC TC                                              22
```

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:10:

```
TGAGACAGAG GATAGGAGAG ACAG                                            24
```

(2) INFORMATION FOR SEQ ID NO:11:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 171..780

(xi) SEQUENCE DESCRIPTION: SEQ ID NO:11:

```
GGGGCTCCGC ACAGCAGGTG AGGCTCTCCT GCCCCATCTC CTTGGGCTGC CCGTGCTTCG      60

TGCTTTGGAC TACCGCCCAG CAGTGTCCTG CCCTCTGCCT GGGCCTCGGT CCCTCCTGCA     120

CCTGCTGCCT GGATCCCCGG CCTGCCTGGG CCTGGGCCTT GGTTCTCCCC ATG ACA        176
                                                       Met Thr
                                                         1

CCA CCT GAA CGT CTC TTC CTC CCA AGG GTG TGT GGC ACC ACC CTA CAC       224
Pro Pro Glu Arg Leu Phe Leu Pro Arg Val Cys Gly Thr Thr Leu His
        5                  10                  15

CTC CTC CTT CTG GGG CTG CTG CTG GTT CTG CTG CCT GGG GCC CAG GGG       272
Leu Leu Leu Leu Gly Leu Leu Leu Val Leu Leu Pro Gly Ala Gln Gly
     20                  25                  30

CTC CCT GGT GTT GGC CTC ACA CCT TCA GCT GCC CAG ACT GCC CGT CAG       320
Leu Pro Gly Val Gly Leu Thr Pro Ser Ala Ala Gln Thr Ala Arg Gln
 35                  40                  45                  50

CAC CCC AAG ATG CAT CTT GCC CAC AGC ACC CTC AAA CCT GCT GCT CAC       368
His Pro Lys Met His Leu Ala His Ser Thr Leu Lys Pro Ala Ala His
             55                  60                  65
```

-continued

```
CTC ATT GGA GAC CCC AGC AAG CAG AAC TCA CTG CTC TGG AGA GCA AAC        416
Leu Ile Gly Asp Pro Ser Lys Gln Asn Ser Leu Leu Trp Arg Ala Asn
         70                  75                  80

ACG GAC CGT GCC TTC CTC CAG GAT GGT TTC TCC TTG AGC AAC AAT TCT        464
Thr Asp Arg Ala Phe Leu Gln Asp Gly Phe Ser Leu Ser Asn Asn Ser
             85                  90                  95

CTC CTG GTC CCC ACC AGT GGC ATC TAC TTC GTC TAC TCC CAG GTG GTC        512
Leu Leu Val Pro Thr Ser Gly Ile Tyr Phe Val Tyr Ser Gln Val Val
100                 105                 110

TTC TCT GGG AAA GCC TAC TCT CCC AAG GCC ACC TCC TCC CCA CTC TAC        560
Phe Ser Gly Lys Ala Tyr Ser Pro Lys Ala Thr Ser Ser Pro Leu Tyr
115                 120                 125                 130

CTG GCC CAT GAG GTC CAG CTC TTC TCC TCC CAG TAC CCC TTC CAT GTG        608
Leu Ala His Glu Val Gln Leu Phe Ser Ser Gln Tyr Pro Phe His Val
             135                 140                 145

CCT CTC CTC AGC TCC CAG AAG ATG GTG TAT CCA GGG CTG CAG GAA CCC        656
Pro Leu Leu Ser Ser Gln Lys Met Val Tyr Pro Gly Leu Gln Glu Pro
                 150                 155                 160

TGG CTG CAC TCG ATG TAC CAC GGG GCT GCG TTC CAG CTC ACC CAG GGA        704
Trp Leu His Ser Met Tyr His Gly Ala Ala Phe Gln Leu Thr Gln Gly
             165                 170                 175

GAC CAG CTA TCC ACC CAC ACA GAT GGC ATC CCC CAC CTA GTC CTC AGC        752
Asp Gln Leu Ser Thr His Thr Asp Gly Ile Pro His Leu Val Leu Ser
180                 185                 190

CCT AGT ACT GTC TTC TTT GGA GCC TTC G                                  780
Pro Ser Thr Val Phe Phe Gly Ala Phe
195                 200
```

(2) INFORMATION FOR SEQ ID NO:12:

(i) SEQUENCE CHARACTERISTICS:
        (A) LENGTH: 203 amino acids
        (B) TYPE: amino acid
        (D) TOPOLOGY: linear (ii) MOLECULE TYPE: protein (xi) SEQUENCE DESCRIPTION: SEQ ID NO:12:

```
Met Thr Pro Pro Glu Arg Leu Phe Leu Pro Arg Val Cys Gly Thr Thr
 1               5                  10                  15

Leu His Leu Leu Leu Leu Gly Leu Leu Leu Val Leu Leu Pro Gly Ala
             20                  25                  30

Gln Gly Leu Pro Gly Val Gly Leu Thr Pro Ser Ala Ala Gln Thr Ala
         35                  40                  45

Arg Gln His Pro Lys Met His Leu Ala His Ser Thr Leu Lys Pro Ala
     50                  55                  60

Ala His Leu Ile Gly Asp Pro Ser Lys Gln Asn Ser Leu Leu Trp Arg
 65                  70                  75                  80

Ala Asn Thr Asp Arg Ala Phe Leu Gln Asp Gly Phe Ser Leu Ser Asn
                 85                  90                  95

Asn Ser Leu Leu Val Pro Thr Ser Gly Ile Tyr Phe Val Tyr Ser Gln
             100                 105                 110

Val Val Phe Ser Gly Lys Ala Tyr Ser Pro Lys Ala Thr Ser Ser Pro
         115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160
```

```
Glu Pro Trp Leu His Ser Met Tyr His Gly Ala Ala Phe Gln Leu Thr
            165                 170                 175

Gln Gly Asp Gln Leu Ser Thr His Thr Asp Gly Ile Pro His Leu Val
        180                 185                 190

Leu Ser Pro Ser Thr Val Phe Phe Gly Ala Phe
        195                 200
```

(2) INFORMATION FOR SEQ ID NO:13:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 171..780

(xi) SEQUENCE DESCRIPTION: SEQ ID NO:13:

```
GGGGCTCCGC ACAGCAGGTG AGGCTCTCCT GCCCCATCTC CTTGGGCTGC CCGTGCTTCG     60

TGCTTTGGAC TACCGCCCAG CAGTGTCCTG CCCTCTGCCT GGGCCTCGGT CCCTCCTGCA    120

CCTGCTGCCT GGATCCCCGG CCTGCCTGGG CCTGGGCCTT GGTTCTCCCC ATG ACA       176
                                                        Met Thr
                                                          1

CCA CCT GAA CGT CTC TTC CTC CCA AGG GTG CGT GGC ACC ACC CTA CAC      224
Pro Pro Glu Arg Leu Phe Leu Pro Arg Val Arg Gly Thr Thr Leu His
          5                  10                  15

CTC CTC CTT CTG GGG CTG CTG CTG GTT CTG CTG CCT GGG GCC CAG GGG      272
Leu Leu Leu Leu Gly Leu Leu Leu Val Leu Leu Pro Gly Ala Gln Gly
     20                  25                  30

CTC CCT GGT GTT GGC CTC ACA CCT TCA GCT GCC CAG ACT GCC CGT CAG      320
Leu Pro Gly Val Gly Leu Thr Pro Ser Ala Ala Gln Thr Ala Arg Gln
 35                  40                  45                  50

CAC CCC AAG ATG CAT CTT GCC CAC AGC ACC CTC AAA CCT GCT GCT CAC      368
His Pro Lys Met His Leu Ala His Ser Thr Leu Lys Pro Ala Ala His
             55                  60                  65

CTC ATT GGA GAC CCC AGC AAG CAG AAC TCA CTG CTC TGG AGA GCA AAC      416
Leu Ile Gly Asp Pro Ser Lys Gln Asn Ser Leu Leu Trp Arg Ala Asn
         70                  75                  80

ACG GAC CGT GCC TTC CTC CAG GAT GGT TTC TCC TTG AGC AAC AAT TCT      464
Thr Asp Arg Ala Phe Leu Gln Asp Gly Phe Ser Leu Ser Asn Asn Ser
     85                  90                  95

CTC CTG GTC CCC ACC AGT GGC ATC TAC TTC GTC TAC TCC CAG GTG GTC      512
Leu Leu Val Pro Thr Ser Gly Ile Tyr Phe Val Tyr Ser Gln Val Val
100                 105                 110

TTC TCT GGG AAA GCC TAC TCT CCC AAG GCC ACC TCC TCC CCA CTC TAC      560
Phe Ser Gly Lys Ala Tyr Ser Pro Lys Ala Thr Ser Ser Pro Leu Tyr
115                 120                 125                 130

CTG GCC CAT GAG GTC CAG CTC TTC TCC TCC CAG TAC CCC TTC CAT GTG      608
Leu Ala His Glu Val Gln Leu Phe Ser Ser Gln Tyr Pro Phe His Val
            135                 140                 145

CCT CTC CTC AGC TCC CAG AAG ATG GTG TAT CCA GGG CTG CAG GAA CCC      656
Pro Leu Leu Ser Ser Gln Lys Met Val Tyr Pro Gly Leu Gln Glu Pro
        150                 155                 160

TGG CTG CAC TCG ATG TAC CAC GGG GCT GCG TTC CAG CTC ACC CAG GGA      704
Trp Leu His Ser Met Tyr His Gly Ala Ala Phe Gln Leu Thr Gln Gly
    165                 170                 175

GAC CAG CTA TCC ACC CAC ACA GAT GGC ATC CCC CAC CTA GTC CTC AGC      752
Asp Gln Leu Ser Thr His Thr Asp Gly Ile Pro His Leu Val Leu Ser
        180                 185                 190
```

```
CCT AGT ACT GTC TTC TTT GGA GCC TTC G                          780
Pro Ser Thr Val Phe Phe Gly Ala Phe
195                 200
```

(2) INFORMATION FOR SEQ ID NO:14:

(i) SEQUENCE CHARACTERISTICS:
        (A) LENGTH: 203 amino acids
        (B) TYPE: amino acid
        (D) TOPOLOGY: linear (ii) MOLECULE TYPE: protein (xi) SEQUENCE DESCRIPTION: SEQ ID NO:14:

```
Met Thr Pro Pro Glu Arg Leu Phe Leu Pro Arg Val Arg Gly Thr Thr
1               5                   10                  15

Leu His Leu Leu Leu Leu Gly Leu Leu Leu Val Leu Leu Pro Gly Ala
                20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
        50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
                100                 105                 110

Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
        130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe
        195                 200
```

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:15:

```
CCAAGGGTGT GTGGCACCA                                            19
```

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear -continued (xi) SEQUENCE DESCRIPTION: SEQ ID NO:16:

CCAAGGGTGC GTGGCACCA                                               19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:17:

CCCACAGCAC CCTCAAACC                                               19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:18:

CCCACAGCAA CCTCAAACC                                               19

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

CCCGTGCTTC GTGCTTTGG                                               19

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

GAGTTCTGCT TGCTGGGGTC TCCT                                         24

METHODS OF DIAGNOSING CLINICAL SUBTYPES OF CROHN'S DISEASE WITH CHARACTERISTIC RESPONSIVENESS TO ANTI-TH1 CYTOKINE THERAPY

RELATED APPLICATIONS

This application is a continuation-in-part of the application Ser. No. 08/837,056 Apr. 11, 1997, now abandoned.

ACKNOWLEDGMENT

This work was supported by USPHS grant DK46763 awarded by the United States Public Health Service. The United States government has certain rights in this invention.

BACKGROUND OF THE INVENTION

1. Field of the Invention

The invention relates generally to the fields of autoimmunity and inflammatory bowel disease and more specifically to serological and genetic methods for predicting the responsiveness of clinical subtypes of Crohn's disease to anti-Th1 cytokine therapies such as anti-TNF-α therapeutics.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Ten percent to fifteen percent of all patients with IBD will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Crohn's disease is a classification representing a number of distinct disease subtypes that affect the gastrointestinal tract and produce similar symptoms. The heterogeneity underlying CD is reflected in variable responses of CD patients to particular treatment strategies: available anti-inflammatory and steroid therapies are effective in treating some patients with CD, while other patients have moderate to severe disease that is refractory to current medical treatment. Anti-Th1 cytokine therapies are a new treatment option for patients with such refractory disease. However, the response to anti-Th1 cytokine therapy, such as an anti-TNF-α therapeutic, is unpredictable. Although about 65% of those with severe Crohn's disease respond dramatically to anti-Th1 cytokine therapy, the remaining 35% of patients with similar clinical characteristics demonstrate a small or negligible response.

Methods for predicting whether a patient with CD will respond to anti-Th1 cytokine therapy would represent a major clinical advance that would aid in the therapeutic management of CD. Such methods would be advantageous in saving the cost of treating those having an unresponsive subtype of CD and would eliminate the disappointment of those needlessly undergoing such therapy. Such methods also would advance medical management of CD by identifying a subgroup of non-responsive patients for whom alternative treatment modalities must be sought. Unfortunately, methods of stratifying CD into clinical subtypes having predictable responses to anti-Th1 cytokine therapy are currently not available. Thus, there is a need for such methods. The present invention satisfies this need and provides related advantages as well.

SUMMARY OF THE INVENTION

The present invention provides genetic and serological methods of diagnosing clinical subtypes of Crohn's disease with characteristic responsiveness to anti-Th1 cytokine therapies such as anti-TNF-α therapeutics. The invention provides, for example, a method of diagnosing a clinical subtype of Crohn's disease having an inferior clinical response to anti-Th1 cytokine therapy by determining whether perinuclear anti-neutrophil antibody (pANCA) is present in a patient with CD, where the presence of pANCA indicates a clinical subtype of CD having an inferior clinical response to anti-Th1 cytokine therapy. The present invention also provides a method of diagnosing a clinical subtype of Crohn's disease having a particular clinical response to anti-Th1 cytokine therapy by determining whether speckling anti-pan polymorphonuclear antibody (SAPPA) is present in a patient with CD, where the presence of SAPPA indicates a clinical subtype of CD having a superior clinical response to anti-Th1 cytokine therapy.

In addition, the invention provides a method of diagnosing a clinical subtype of Crohn's disease having an inferior clinical response to anti-Th1 cytokine therapy by determining the presence or absence of a TNFa10b4c1d3e3 haplotype in a patient with CD, where the presence of the TNFa10b4c1d3e3 haplotype indicates a clinical subtype of CD having an inferior clinical response to anti-Th1 cytokine therapy. The present invention also provides a method of diagnosing a clinical subtype of Crohn's disease having an inferior clinical response to anti-Th1 cytokine therapy by determining the presence or absence of a TNFa11b4c1d3e3 haplotype in a patient with CD, where the presence of the TNFa11b4c1d3e3 haplotype indicates a clinical subtype of CD having an inferior clinical response to anti-Th1 cytokine therapy.

The invention further provides a method of diagnosing a clinical subtype of CD having an inferior clinical response to anti-Th1 cytokine therapy by determining the presence or absence of a homozygous TNF-β 1111 haplotype at the TNFc, aa13L, aa26 and NcoI loci in a patient with CD, where the presence of the homozygous TNF-β 1111 haplotype indicates a clinical subtype of CD having an inferior clinical response to anti-Th1 cytokine therapy.

In addition, there is provided a novel TNF-β nucleotide sequence SEQ ID NO: 13, which has a polymorphism at the nucleotide corresponding to amino acid 13 of the TNF-β leader sequence. The invention also provides an allele-specific oligonucleotide primer for detection of the polymorphic TNF-β sequence SEQ ID NO: 13, which has at least 15 nucleotides of SEQ ID NO: 13 shown in FIG. 4B, including the nucleotide at position 207 of SEQ ID NO: 13.

Also provided herein are combined serological and genetic methods of diagnosing a clinical subtype of Crohn's disease having a particular clinical response to anti-Th1 cytokine therapy. The invention provides a method of diagnosing a clinical subtype of CD having a particular clinical response to anti-Th1 cytokine therapy by determining whether SAPPA is present in a patient with CD, determining whether pANCA is present in the patient, determining the presence or absence of a TNFa10b4c1d3e3 haplotype in the patient and determining the presence or absence of a TNFa11b4c1d3e3 haplotype in the patient, where the presence of SAPPA indicates a clinical su b type of CD having a superior clinical response to anti-Th1 cytokine therapy, the presence of pANCA indicates a clinical subtype of CD having an inferior clinical response to anti-Th1 cytokine therapy, the presence of the TNFa10b4c1d3e3 haplotype independently indicates a clinical subtype of CD having an inferior clinical response to anti-Th1 cytokine therapy and the presence of the TNFa11b4c1d3e3 haplotype independently indicates a clinical subtype of CD having an inferior clinical response to anti-Th1 cytokine therapy.

In addition, the present invention provides kits for diagnosing a clinical subtype of CD having a particular clinical response to anti-Th1 cytokine therapy. The kits of the invention include neutrophil and one or more oligonucleotide primers complementary to a nucleotide sequence flanking a TNF microsatellite locus selected from the group consisting of TNFa, TNFb, TNFc, TNFd and TNFe. The kits can include, for example, neutrophil and pairs of oligonucleotide primers complementary to nucleotide sequences flanking each of the TNFa, TNFb, TNFc, TNFd and TNFe loci. The neutrophil can be, for example, alcohol-fixed neutrophil. If desired, one or more secondary antibodies selective for ANCA also can be included in the kits of the invention.

BRIEF DESCRIPTION OF THE DRAWINGS

FIGS. 4A–C shows the relative locations of six biallelic polymorphisms within the TNF-α and TNF-β genes and the sequence of the TNF-β aa13L polymorphism. FIG. 4A. The two biallelic −238 and −308 polymorphisms are shown within the TNF-α promoter. Within the TNF-β gene, the NcoI restriction fragment length polymorphism (RFLP) and TNFc loci are located within the first intron, and the aa13L and aa26 polymorphisms are located within exon 1. FIG. 4B. The fill nucleotide sequence (SEQ ID NO: 11) and amino acid sequence (SEQ ID NO: 12) of the wild type TNF-β cDNA are shown. The nucleotide sequence of the mutant TNF-β cDNA (SEQ ID NO: 13) differs from the wild type sequence at nucleotide position 207, where C is substituted for T. The amino acid sequence of the mutant TNF-β cDNA (SEQ ID NO: 14) differs from the wild type sequence at amino acid 13 of the leader sequence (aa13L), where arginine is substituted for cysteine.

FIG. 5A. Patients treated with cA2 were subtyped according to their genotype at each of four biallelic TNF-β loci: TNFc, aa13L, aa26 and NcoI. For each of the four loci, "1" indicates the common allele, and "2" indicates the rare allele. The percentage of CD patients with a clinical response to cA2 at 4 weeks is shown for each of the subtypes. FIG. 5B. ANCA-positive CD patients were subtyped according to genotype at aa13L, with the designation "1" indicating the common "T" allele and "2" indicating the rare "C" allele.

FIG. 6A. The percentage of CD patients with a clinical response to cA2 was determined at 4 weeks. Patients were subtyped according to their haplotype at the TNFc, aa13L, aa26 and NcoI loci. The designation "1111/1111" indicates a patient having a homozygous genotype with two copies of the haplotype of common alleles at the TNFc, aa13L, aa26 and NcoI loci. The designation "1111/X" indicates a patient having a heterozygous genotype with one copy of the haplotype of common alleles at the TNFc, aa13L, aa26 and NcoI loci. The designation "X/X" indicates a patient lacking the haplotype of common alleles at the TNFc, aa13L, aa26 and NcoI loci. FIG. 6B. Shown is the percentage of ANCA-positive CD patients subtyped according to homozygosity at the TNF-β four locus haplotype and according to pANCA or SAPPA status.

DETAILED DESCRIPTION OF THE INVENTION

The present invention provides, in a method of treating a patient with Crohn's disease (CD) with anti-Th1 cytokine therapy, an improvement including determining whether perinuclear anti-neutrophil antibody (pANCA) is present in the patient with CD, where the presence of pANCA indicates a clinical subtype of CD having an inferior clinical response to anti-Th1 cytokine therapy.

The invention also provides a method of diagnosing a clinical subtype of Crohn's disease having an inferior clinical response to anti-Th1 cytokine therapy by determining whether pANCA is present in a patient with CD, where the presence of pANCA indicates a clinical subtype of CD having an inferior clinical response to anti-Th1 cytokine therapy.

The present invention further provides, in a method of treating a patient with Crohn's disease with anti-Th1 cytokine therapy, an improvement including determining whether speckling anti-pan polymorphonuclear antibody (SAPPA) is present in the patient with CD, where the presence of SAPPA indicates a clinical subtype of CD having a superior clinical response to anti-Th1 cytokine therapy.

In addition, there is provided a method of diagnosing a clinical subtype of Crohn's disease having a particular clinical response to anti-Th1 cytokine therapy by determining whether SAPPA is present in a patient with CD, where the presence of SAPPA indicates a clinical subtype of CD having a superior clinical response to anti-Th1 cytokine therapy.

As described herein, approximately 35% of Crohn's disease patients do not respond to a first infusion of the anti-TNF-α antibody cA2, a representative anti-Th1 cytokine therapy. These non-responsive CD patients represent a subgroup with disease refractory to anti-Th1 cytokine therapy as evidenced by the results provided in Example I. These results show that the subgroup of Crohn's disease patients that did not respond to a first infusion of the anti-TNF-α antibody cA2 was much less likely to respond to a second infusion than the general population of CD patients. In particular, only 28% of those initially failing to respond were responsive to the second infusion at 12 weeks, as compared to 56% of those initially treated with placebo (see Table 6). These results provide evidence for a clinical subtype of Crohn's Disease that is characterized as having an inferior clinical response to anti-Th1 cytokine therapy.

Figure 2:
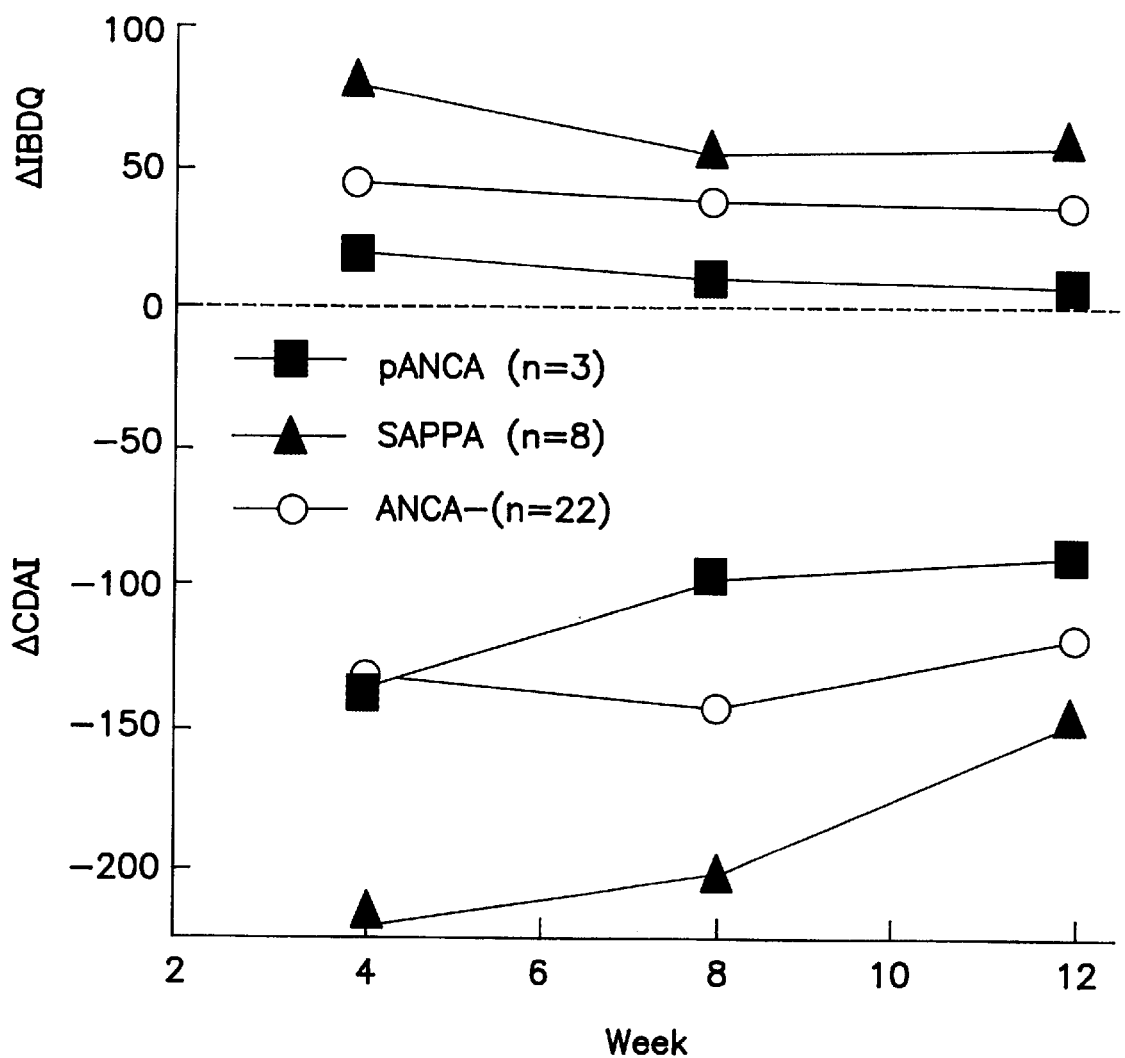
FIG. 2 shows the magnitude and duration of response to the cA2 antibody for the pANCA-positive and SAPPA-positive subtypes of Crohn's disease. ΔIBDQ and ΔCDAI were assayed at two week intervals over a period of 12 weeks after treatment with cA2.

Provided herein are serological methods of diagnosing clinical subtypes of CD having an inferior or superior clinical response to anti-Th1 cytokine therapy, such as an anti-TNF-α therapeutic, an anti-IFN-γ therapeutic, an anti-IL-12 therapeutic or IL-10. As set forth in Example II and summarized in Table 8, the presence of perinuclear anti-neutrophil antibodies (pANCA) in a patient with CD defines a clinical subtype of CD characterized by an inferior clinical response to anti-Th1 cytokine therapy. While the percentage of cA2-treated patients going into remission in the general population was 25%, the clinical subtype characterized by the presence of pANCA had a significantly reduced remission rate of only about 11%. As shown in FIG. 2, the response of the pANCA-positive subtype of CD was diminished in magnitude and duration in comparison with other clinical subtypes of CD. In contrast, the presence of SAPPA was diagnostic of a subtype of CD with a superior clinical response to anti-Th1 cytokine therapy: this subtype had a remission rate of about 42% as compared to the 25% remission rate seen in the general population of cA2-treated CD patients. Moreover, both the magnitude and duration of the response were augmented in the SAPPA-positive CD patient subtype (see FIG. 2). These results were supported by significant reductions in the Crohn's disease activity index and the inflammatory bowel disease quality of life index. Thus, the presence of pANCA predicts an inferior clinical response to anti-Th1 cytokine therapy while the presence of SAPPA predicts a superior clinical response to this therapy.

Inflammatory bowel disease has been classified into the broad categories of Crohn's disease and ulcerative colitis. Crohn's disease, or regional enteritis, is a disease of chronic inflammation that can involve any part of the gastrointestinal tract. Commonly the distal portion of the small intestine (ileum) and cecum are affected. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of CD are abdominal pain, diarrhea and recurrent fever. CD is commonly associated with intestinal obstruction or fistula, which is an abnormal passage between diseased loops of bowel, for example. Crohn's disease also can include extra-intestinal complications such as inflammation of the eye, joints and skin; liver disease; kidney stones or amyloidosis. CD is also associated with an increased risk of intestinal cancer.

Several features are characteristic of the pathology of Crohn's disease. The inflammation associated with CD, known as transmural inflammation, involves all layers of the bowel wall. Thickening and edema, for example, typically appear throughout the bowel wall, with fibrosis also present in long-standing disease. The inflammation characteristic of CD also is discontinuous with segments of inflamed tissue, known as "skip lesions," separated by apparently normal intestine. Furthermore, linear ulcerations, edema, and inflammation of the intervening tissue lead to a "cobblestone" appearance of the intestinal mucosa, which is distinctive of CD.

A hallmark of Crohn's disease is the presence of discrete aggregations of inflammatory cells, known as granulomas, which are generally found in the submucosa. About half of Crohn's disease cases display the typical discrete granulomas, while others show a diffuse granulomatous reaction or nonspecific transmural inflammation. As a result, the presence of discrete granulomas is indicative of CD, although the absence granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J. B. Lippincott Company (1994), which is incorporated herein by reference).

As used herein, the term "patient with Crohn's disease" is synonymous with "patient with CD" and means a patient having a characteristic feature from at least two of the following categories: clinical, endoscopic, radiographic and histopathologic. As used herein, a characteristic clinical feature is perforating or fistulizing disease; or an obstructive symptom secondary to small bowel stenosis or stricture. As used herein, a characteristic endoscopic feature is a deep linear or serpiginous ulceration; a discrete ulcer in normal-appearing mucosa; cobblestoning; or discontinuous or asymmetric inflammation. As used herein, a characteristic radiographic feature is segmental disease (skip lesion); a small bowel or colon stricture; stenosis or fistula. As used herein, a characteristic histopathologic feature is submucosal or transmural inflammation; multiple granulomas; marked focal cryptitis or focal chronic inflammatory infiltration within and between biopsies; or a skip lesion, including histologic rectal sparing in the absence of local therapy.

Crohn's disease is a chronic inflammatory disorder characterized by transmural, granulomatous inflammation, involving any part of the gastrointestinal tract in a discontinuous fashion. Patients with Crohn's disease present with a wide spectrum of clinical features and with great variation in disease course. Although the clinical, endoscopic, and histopathologic criteria described above have been developed as guides for diagnosing a patient with Crohn's disease, such criteria may not be specific enough to adequately guide medical and surgical treatment strategies.

A number of therapies have been used for the treatment of Crohn's disease with varying success. Mild Crohn's disease may be responsive to first line therapies such as the anti-inflammatory 5-aminosalicylic acid (5-ASA); however, the majority of patients will relapse and require corticosteroid therapy. Immunomodulatory therapy with azathioprine or 6-mercaptopurine (6-MP) is effective in some patients with moderate disease. In addition, methotrexate (MTX) and cyclosporine can be used to treat patients with severe, persistent disease who either do not respond to corticosteroid therapy or who experience recurrence of symptoms upon steroid taper (see Plevy and Targan, In: Targan and Shanahan, *Inflammatory Bowel Disease: From Bench to Bedside* Williams and Wilkens, 1993, pp. 582–609; and Hanauer, *New Engl. J. Med.* 334(13):841–848 (1996), each of which is incorporated herein by reference). In spite of available therapies, a significant percentage of Crohn's disease patients have disease that is not alleviated by any combination of standard medications. Anti-TNF-α therapy is a new treatment option for those patients having moderate to severe disease that persists despite treatment with steroids, azathioprine or 6-MP, and 5-ASA.

An imbalance of cytokine production or activity can be important in the chronic mucosal inflammatory processes manifesting as Crohn's disease. In particular, the Crohn's disease mucosal inflammatory process may reflect a shift in the balance of T-cell cytokine production toward the subclass of T-cells designated T helper 1 (Th1) (Mullin et al., *Gastroenterology* 102:1528 (1992) and Fuss et al., *J. Immunol.* 157:1261–1270 (1996)). Rodent models of chronic colitis indicate that compounds capable of down-regulating cytokine production from Th1 cells can profoundly ameliorate or eliminate chronic intestinal inflammation. For example, in scid mice with inflammatory bowel disease induced by reconstitution with CD45RB$^{hi}$ CD4+ T cells, administration of neutralizing anti-INFγ or anti-TNF-α monoclonal antibodies can prevent the onset and reduce the severity of inflammation (Powrie et al., *Immunity* 1:553–562 (1994), which is incorporated herein by reference). Proinflammatory cytokines produced by Th1 cells, including IFNγ, IL-2 and TNF, also have been implicated in development of Crohn's disease in humans. For example, increased production of TNF-α is evident in the mucosa of Crohn's disease patients (MacDonald et al., *Clin. Exp. Immunol.* 81:301–305 (1990) and Murch, *Gut* 34:1705–1709 (1993)).

Because TNF-α has been shown in some systems to be a co-factor in stimulating Th1 cytokine production, this cytokine is a particularly attractive target for therapeutic intervention (Mossman and Coffman, *Ann. Rev. Immunol.* 7:145–173 (1989) and Pirmez et al., *J. Clin. Invest.* 91:1390–1395 (1993)). A recent open-label trial has shown that, in a small group of patients with Crohn's disease unresponsive to standard medication, the majority responded to treatment with cA2, a neutralizing anti-TNF-α chimeric antibody known to inhibit TNF-induced interleukin-6 release and endothelial procoagulant and adhesion molecule expression (van Dullemen et al., *Gastroenterol.* 109:129–135 (1995), which is incorporated herein by reference).

Thus, anti-Th1 cytokine therapy such as treatment with the anti-TNF-α neutralizing antibody cA2 can help some patients with Crohn's disease unresponsive to standard medications. As disclosed herein, the methods of the invention can be used to predict which Crohn's disease patients will respond to anti-Th1 cytokine therapy. The methods of the invention are useful, for example, in saving the cost of treating those patients who will be unresponsive to such therapy and in eliminating the disappointment of those needlessly undergoing treatment. Such methods also would advance medical management of CD by identifying the poorly responsive clinical subtypes for whom alternative treatment modalities must be sought. Conversely, the methods of the invention for diagnosing a clinical subtype that will have a superior clinical response to anti-Th1 cytokine therapy are useful in identifying those patients who can be successfully treated.

As used herein, the term "anti-Th1 cytokine therapy" means any therapy, including a small molecule drug, protein, peptide, nucleic acid, antisense nucleic acid, antibody, or combination thereof, that decreases the level or activity of one or more proinflammatory cytokines produced by T helper 1 (Th1) cells, or that decreases the activity of a pathway promoted by one or more proinflammatory cytokines produced by Th1 cells, relative to the level or activity of cytokines produced by non-Th1 cells. Anti-Th1 cytokine therapy can decrease, for example, the expression, effective concentration, bioavailability or activity of one or more Th1 proinflammatory cytokines by a variety of mechanisms. For example, such therapy can decrease the level of Th1 cytokine expression by decreasing the rate of Th1 cytokine transcription or translation; shortening mRNA or protein half-life; or increasing Th1 cytokine clearance or sequestration. An inhibitor of a transcription factor important for expression of a Th1 cytokine, such as an NF-κB antisense therapeutic, is an example of an anti-Th1 cytokine therapy as defined herein. Treatment with IL-10 is another example of anti-Th1 cytokine therapy as defined herein, treatment with IL-10 can reduce the expression of the Th1 cytokine TNF-α. Anti-Th1 cytokine therapy also can decrease Th1 cytokine activity by neutralizing the activity of a Th1 cytokine or preventing its ability to signal through its cognate receptor without altering the level of cytokine expression.

Anti-Th1 cytokine therapy, as described above, can reduce the level or activity of one or more of a number of proinflammatory cytokines produced by Th1-cells relative to the level or activity of cytokines produced by non-Th1 cells. For example, anti-Th1 cytokine therapy can reduce the level or activity of tumor necrosis factor-alpha (TNF-α); gamma-interferon (IFN-γ); interleukin-2 (IL-2); or another proinflammatory cytokine produced by a Th1 cell. Furthermore, anti-Th1 cytokine therapy can reduce the level or activity of interleukin-6 (IL-6) or interleukin-12 (IL-12). Preferably, anti-Th1 cytokine therapy reduces the level or activity of one or more Th1 proinflammatory cytokines in a human.

One skilled in the art understands that anti-Th1 cytokine therapy can function directly or indirectly. For example, anti-Th1 cytokine therapy can function indirectly to decrease the level of a Th1 cytokine by reducing the number or activity of Th1 cells. In addition, anti-Th1 cytokine therapy can be a soluble cytokine receptor or soluble cytokine receptor fusion protein, such as p55 TNF receptor-IgG or p75 TNF receptor-IgG, which blocks cytokine activity by competing with endogenous receptor (see, for example, Fenner, *Z. Rhematol.* 54:158–164 (1995); Selmaj and Raine, *Neurol.* 45:S44–49 (1995); and Williams et al., *Immunol.* 84:433–439 (1995), each of which is incorporated herein by reference).

Antibodies that neutralize a proinflammatory cytokine also are examples of anti-Th1 cytokine therapy that can be used to treat patients with Crohn's disease; the response of a patient to such neutralizing antibodies can be predicted using the methods of the invention. Anti-Th1 cytokine therapy, as defined herein, includes antibodies that neutralize TNF-α, IFN-γ, IL-2 or IL-12 (see, for example, Van Dullleman et al., supra, 1995; Fenner, supra, 1995; Selmaj and Raine, supra, 1995; Exley et al., *Lancet* 1275–1277 (1990); and Powrie et al., *Immunity* 1:553–562 (1994), each of which is incorporated herein by reference). The chimeric A2 monoclonal antibody (cA2), which is a chimeric mouse-human IgG1 antibody that binds to both soluble and transmembrane human TNF-α with high affinity and specificity, is an example of anti-Th1 cytokine therapy as defined herein (Knight et al., *Mol. Immunol.* 30:1443–1453 (1993), which is incorporated herein by reference). Monoclonal antibody cA2 neutralizes the functional activity of TNF-α in a wide variety of bioassays by blocking the binding of TNF-α to the p55 and p75 TNF receptors (Siegel et al., *Cytokine* 7:15–25 (1995), which is incorporated herein by reference). An anti-Th1 cytokine therapy also can be an anti-IFN-γ antibody such as the XMG1.2 anti-mouse IFN-γ monoclonal antibody described in Cherwinski et al., *J. Exp. Med.* 166:1229–1244 (1987), which is incorporated herein by reference, or the XT-22 anti-mouse TNF-α and β monoclonal antibody described in Abrams et al., *J. Immunol.* 140:131–137 (1988), which is incorporated herein by reference.

The present invention also provides a method of diagnosing a clinical subtype of Crohn's disease having an inferior clinical response to anti-Th1 cytokine therapy by determining whether pANCA is present in a patient with CD by obtaining a serum sample from the patient with CD, determining by non-histological means whether anti-neutrophil cytoplasmic antibody (ANCA) is detectable in patient sera diluted at least about 100-fold and assaying for the presence or absence of a pANCA staining pattern, where detection of ANCA in patient sera diluted at least about 100-fold and the presence of a pANCA staining pattern indicate the presence of pANCA, provided that the detection of ANCA is not by histological means.

As used herein, the term "inferior clinical response" means the clinical response of a CD patient or subpopulation of patients to a therapy that is significantly lower than the average clinical response of a non-stratified population of CD patients to the same therapy. The term "superior clinical response" means a clinical response of a CD patient or subpopulation of patients to a therapy that is significantly greater than the average clinical response of a non-stratified population of CD patients to the same therapy. The term "particular clinical response," as defined herein, means a clinical response that is either inferior or superior. A clinical response can be measured by a change in clinical disease as indicated, for example, by a change in the Crohn's disease activity index (CDAI), the inflammatory bowel disease quality of life index (IBDQ), or a change in remission rate.

The Crohn's disease activity index (CDAI) incorporates eight Crohn's disease related variables: the number of liquid or very soft stools; abdominal pain or cramping; general well being; extra-intestinal manifestations of Crohn's disease; abdominal mass; use of antidiarrheal drugs; hematocrit; and body weight. Together, these items yield a composite score ranging from 0 to approximately 600 with higher scores indicating more disease activity. Patients with a score of less than 150 are considered to be in remission, while patients with a score of above 450 are severely ill.

The IBDQ is a 32-item questionnaire that evaluates quality of life across four dimensions: bowel parameters such as loose stools or abdominal pain; systemic parameters such as fatigue or altered sleep pattern; social parameters such as work attendance and the need to cancel social events; and emotional variables such as anger, depression or irritability. The IBDQ questionnaire yields scores ranging from 32 to 224, with higher scores indicating better quality of life. The scores of patients in remission usually range from 170 to 190.

The levels of C-reactive protein (CRP) can be used as an indicator of inflammatory activity that confirms a clinical response. Although normal serum levels of CRP are between about 0.02 and 0.1 mg/ml in humans, serum CRP levels range from 2 to 3 mg/ml during an inflammatory response. Serum CRP levels correlate with clinical progression in Crohn's disease (Targan and Shanahan, supra., 1996).

The methods of the invention for diagnosing clinical subtypes of Crohn's disease involve determining whether pANCA or SAPPA is present in a patient having CD. Such serum antibodies to cytoplasmic components of a neutrophil (ANCA) can be detected, for example, using indirect immunofluorescence microscopy of alcohol-fixed neutrophils. As disclosed herein, ANCA activity is divided into several broad categories: perinuclear to nuclear staining or cytoplasmic staining with perinuclear highlighting (pANCA); diffuse staining with speckling across the entire neutrophil (SAPPA); and cytoplasmic neutrophil staining without perinuclear highlighting (cANCA). The term "anti-neutrophil cytoplasmic antibody" is synonymous with "ANCA" and encompasses pANCA, SAPPA and cANCA.

As used herein, the term "ANCA-positivity" and means the presence of ANCA, whether pANCA, SAPPA or cANCA. The term "low level ANCA-positivity" means a level of ANCA-positivity less than about 40% of the level of ANCA-positivity of well characterized pANCA-positive UC sera.

As used herein, the term "perinuclear anti-neutrophil cytoplasmic antibody" is synonymous with "pANCA" and refers to an antibody that reacts specifically with a neutrophil to give perinuclear to nuclear staining or cytoplasmic staining with perinuclear highlighting. The term pANCA-positive, when used in reference to a patient, means a patient having pANCA. The term "pANCA staining pattern" means a perinuclear to nuclear staining pattern or a cytoplasmic staining pattern with perinuclear highlighting that distinguishes pANCA from, for example, SAPPA and cANCA. The pANCA staining pattern is shown in panel (b) of FIG. 1.

As used herein, the term "speckling anti-pan polymorphonuclear antibody" is synonymous with "SAPPA" and refers to an anti-neutrophil antibody that gives low level ANCA-positivity and that reacts specifically with a neutrophil to give diffuse staining with speckling across the entire cell. The term "SAPPA-positive," when used in reference to a patient, means a patient having SAPPA. The term "SAPPA staining pattern" means a diffuse staining pattern with speckling across the entire surface of a neutrophil that distinguishes SAPPA from, for example, pANCA and cANCA. The SAPPA staining pattern is shown in panel (c) of FIG. 1.

Previous studies have consistently shown ANCA reactivity in a small portion of patients with Crohn's disease although these antibodies are elevated more frequently in patients with ulcerative colitis. The reported prevalence in CD varies from 0 to 43% with most studies reporting that 10 to 30% of CD patients express ANCA (see, for example, Saxon et al., J. Allergy Clin. Immunol. 86:202–210 (1990); Cambridge et al., Gut 33:668–674 (1992); Pool et al., Gut 3446–50 (1993); and Brokroelofs et al., Dig. Dis. Sci. 39:545–549 (1994).

The pANCA-positive subtype of Crohn's disease does not correlate with traditional CD subgroups based on, for example, location of disease (small bowel only, colon only, or small bowel and colon); extent of disease; duration of illness; disease activity; medical therapy; or surgical history (Cambridge et al., supra, 1992; Pool et al., supra, 1993; Brokroelofs et al., supra, 1994). Previous work has suggested that ANCA expression in CD patients may be related to colonic disease (Sung et al., Dig. Dis. Sci. 39:886–892 (1994); Proujansky et al., J. Pediatr. Gastroenterol. Nutr. 17:193–197 (1993); and Patel et al., Br. J. Surg. 81:724–726 (1994)). However, the majority of CD patients with colonic disease are not pANCA-positive, and the presence of colonic disease alone does not characterize the pANCA-positive subtype of CD patients. The presence of pANCA in CD can be diagnostic of features of ulcerative colitis such as left-sided colonic disease in which the distal portion of the colon is more severely inflamed than the proximal portion and clinical symptoms of left-sided colonic inflammation such as rectal bleeding.

In the methods of the invention, the presence of pANCA or the presence of SAPPA can be determined as described in Example III. The presence of pANCA or the presence of SAPPA can be determined using a sample obtained from any biological fluid having ANCA such as, for example, whole blood, plasma or other bodily fluid or tissue having ANCA, preferably serum. When multiple samples are used in an assay for determining the presence of pANCA or SAPPA, it is preferred that the same type of biological fluid or tissue is used for each sample.

A serum sample diluted at least about 100-fold is particularly useful in the methods of the invention. As disclosed herein, the presence of pANCA in a patient with CD is preferably determined by obtaining a serum sample from the patient with CD; determining whether ANCA is detectable in patient sera diluted at least about 100-fold and assaying for the presence or absence of a pANCA staining pattern, where detection of ANCA in patient sera diluted at least about 100-fold and the presence of a pANCA staining pattern indicate the presence of pANCA, provided that the detection of ANCA is not by histological means.

Numerous studies have used indirect immunofluorescence alone to detect the presence of serum ANCA, thereby determining whether pANCA is present simply on the basis of a pANCA staining pattern. Furthermore, where a quantitative assay has been relied upon in addition to a pANCA staining pattern, detection of ANCA has been determined using a relatively high concentration of patient sera, such as a 20-fold or 40-fold dilution of sera, for example. In contrast, the present invention is directed to the discovery that the presence of pANCA, as determined rigorously by both detection of ANCA in patient sera diluted at least about 100-fold and the presence of a pANCA staining pattern, is diagnostic of a clinical subtype of CD having an inferior clinical response to anti-Th1 cytokine therapy, provided that detection of ANCA in patient sera is not by histological means.

As used herein, the term "histological means," when used in reference to detection of ANCA or detection of a first complex of antigen and ANCA, refers to a technique for studying the structure of a cell or tissue using staining and microscopy. Histological means, which encompass techniques such as immunocytochemistry and indirect immunofluorescence, can distinguish pANCA, SAPPA and cANCA staining patterns and, thus, are useful in assaying for the presence or absence of a pANCA or SAPPA staining pattern, for example. However, histological means, which typically are subjective, are not useful for rigorously determining whether ANCA is detectable in patient sera diluted at least about 100-fold. The use of histology, as defined herein, for determining whether ANCA is detectable in patient sera diluted at least about 100-fold or the level of ANCA-positivity in patient sera diluted at least about 100-fold is explicitly excluded from the present invention. Similarly, the present invention explicitly excludes the use of histological means to detect the presence or absence of a first complex of antigen and ANCA.

It is recognized that determining whether ANCA is detectable in patient sera diluted at least about 100-fold can be performed prior to, following or concurrent with assaying for the presence or absence of a pANCA or SAPPA staining pattern. Thus, for example, an immunofluorescence assay for the presence of a pANCA staining pattern followed by an enzyme-linked immunosorbent assay for determining whether ANCA is detectable in patient sera diluted at least about 100-fold is encompassed within the methods of the invention. Similarly, an immunofluorescence assay for the presence of a SAPPA staining pattern followed by an enzyme-linked immunosorbent assay for determining the level of ANCA-positivity in patent sera diluted at least about 100-fold is encompassed within the methods of the invention.

Methods of determining whether ANCA is detectable and the level of ANCA-positivity in patient sera diluted at least about 100-fold are well known in the art (Harlow and Lane, *Antibodies: A Laboratory Manual* New York: Cold Spring Harbor Laboratory (1988), which is incorporated herein by reference). For example, ANCA can be detected in patient sera using a detectable reagent such as a secondary antibody labeled with a detectable enzymatic, radioisotopic, fluorescent or chemiluminescent marker. Particularly useful methods include a quantitative assay such as an immunoassay, in which an antibody selective for ANCA is used to detect ANCA in patient sera and to determine, if desired, the level of ANCA-positivity. A radioimmunoassay (RIA) or enzyme-linked immunosorbent assay (ELISA), for example, is encompassed within the invention. As discussed above, the present invention explicitly excludes the use of histological means such as immunocytochemistry or immunofluorescence for determining whether ANCA is present in patient sera diluted at least about 100-fold and for determining the level of ANCA-positivity in patient sera diluted at least about 100-fold.

An enzyme-inked immunosorbent assay (ELISA) can be useful in determining whether ANCA is present in patient sera diluted at least about 100-fold. For example, a fixed neutrophil ELISA for detection of ANCA in patient sera diluted 100-fold is described in Example III. An enzyme that is linked to a secondary antibody selective for ANCA can be, for example, horseradish peroxidase (HRP), alkaline phosphatase (AP), β-galactosidase or urease. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm, or a urease detection system can be used with a substrate such as urea-bromocresol purple (Sigma Immunochemicals, St. Louis, Mo.). A secondary antibody linked to an enzyme is a detectable reagent useful in an ELISA and can be obtained from a number of commercial sources. For example, goat F(ab')2 anti-human IgG-alkaline phosphatase can be purchased from Jackson Immuno-Research (West Grove, Pa.).

A radioimmunoassay also can be useful in determining whether ANCA is present in patient sera diluted at least about 100-fold and the level of ANCA-positivity in patient sera diluted at least about 100-fold. A radioimmunoassay using, for example, an iodine-125 labeled secondary antibody (Harlow and Lane, supra, 1988) is encompassed within the invention.

A secondary antibody labeled with a chemiluminescent marker also can be useful for determining whether ANCA is present in patient sera diluted at least about 100-fold and for determining the level of ANCA-positivity in patient sera diluted at least about 100-fold. Such a chemiluminescent secondary antibody is convenient for sensitive, non-radioactive detection of ANCA and can be obtained commercially from various sources such as Amersham Lifesciences, Inc. (Arlington Heights, Ill.).

In addition, a detectable reagent labeled with a fluorochrome can be useful in determining whether ANCA is present in patient sera diluted at least about 100-fold and the level of ANCA-positivity in patient sera diluted at least about 100-fold. Appropriate fluorochromes include, for example, DAPI, fluorescein, Hoechst 33258, R-phycocyanin, B-phycoerythrin, R-phycoerythrin, rhodamine, Texas red or lissamine. A particularly useful fluorochrome is fluorescein or rhodamine. A secondary antibody linked to a fluorochrome is a particularly useful detectable reagent and can be obtained commercially. For example, goat F(ab')2 anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine-125; or a fluorometer to detect fluorescence in the presence of light of a certain wavelength. For detection of enzyme-linked reagents, a quantitative analysis of the amount of ANCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Immunoassays using a secondary antibody selective for ANCA are particularly useful in the methods of the invention. As used herein, the term "antibody" means a population of immunoglobulin molecules, which can be polyclonal or monoclonal and of any isotype. As used herein, the term antibody encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

As used herein, the term "secondary antibody selective for ANCA" means an antibody, or combination of antibodies, which binds ANCA. Preferably, such a secondary antibody does not compete with neutrophil for binding to ANCA. A secondary antibody can be an anti-ANCA antibody that binds any epitope of ANCA. A particularly useful secondary antibody is an anti-IgG antibody having specificity for the class determining portion of ANCA. A useful secondary antibody is specific for the species of the ANCA to be detected. For example, if human serum is the sample to be assayed, mouse anti-human IgG can be a useful secondary antibody. A combination of different antibodies, which can be useful in the methods of the invention, also is encompassed within the meaning of the term secondary antibody, provided that at least one antibody of the combination binds ANCA.

A secondary antibody useful in an immunoassay of the invention can be obtained commercially or by techniques well known in the art. Such an antibody can be a polyclonal or, preferably, monoclonal antibody that binds ANCA selectively. For example, IgG reactive polyclonal antibodies can be prepared using IgG or Fc fragments of IgG as an immunogen to stimulate the production of antibodies in the antisera of an animal such as a rabbit, goat, sheep or rodent, for example (Harlow and Lane, supra, 1988).

A monoclonal antibody useful in the practice of the invention can be obtained from a number of commercially available sources. In addition, an immunogen useful to generate a monoclonal antibody that binds ANCA selectively can be, for example, human IgG or a Fc fragment of human IgG, ANCA or a Fab fragment of ANCA. A hybridoma that produces a monoclonal selective for ANCA can be identified by screening hybridoma supernatants for the presence of antibodies that bind ANCA specifically (Harlow, supra, 1988). For example, such a screening method can be a radioimmunoassay or enzyme-linked immunosorbent assay using neutrophil and pANCA-positive sera, for example.

Methods of assaying for the presence or absence of a pANCA staining pattern or a SAPPA staining pattern also are well known in the art and are set forth in Example III. Methods of cell staining using, for example, neutrophil, are useful for determining the subcellular localization of ANCA reactivity, thereby differentiating pANCA from SAPPA and cANCA. Immunocytochemistry or immunofluorescence are particularly useful for assaying for the presence of a pANCA staining pattern or a SAPPA staining pattern (Harlow and Lane, supra, 1988). An enzyme-labeled or fluorochrome labeled secondary antibody that binds ANCA selectively, such as described above, can be useful in such methods. For example, indirect immunofluorescence readily can be performed by incubating methanol-fixed neutrophil with a 1:20 dilution of human sera and detecting the complex formed with fluorescein-labeled F(ab')2 γ chain secondary antibody. The presence of the pANCA or SAPPA staining pattern in the stained neutrophils can be visualized using fluorescence microscopy as described in Saxon et al., supra, 1990, or in Example III.

In one embodiment, the invention provides a method of diagnosing a clinical subtype of CD having an inferior clinical response to anti-Th1 cytokine therapy by determining whether pANCA is present in a patient with CD by obtaining a serum sample from the patient with CD; contacting the serum sample diluted at least about 100-fold with antigen specific for ANCA under conditions suitable to form a first complex of antigen and ANCA; detecting the presence or absence of the first complex; contacting an appropriate dilution of the serum sample with antigen specific for ANCA under conditions suitable to form a second complex of neutrophil and ANCA; and assaying for the presence or absence of a pANCA staining pattern by detecting the presence or absence of the second complex, where the presence of the first complex and the presence of a pANCA staining pattern indicate the presence of pANCA, provided that detection of the first complex is not by histological means.

The invention also provides a method of diagnosing a clinical subtype of Crohn's disease having a particular clinical response to anti-Th1 cytokine therapy by determining the presence of SAPPA in a patient with CD by obtaining a serum sample from the patient with CD, contacting the serum sample diluted at least about 100-fold with antigen specific for ANCA under conditions suitable to form a first complex of antigen and ANCA, detecting the presence or absence of the first complex, contacting an appropriate dilution of the serum sample with antigen specific for ANCA under conditions suitable to form a second complex of antigen and ANCA, and assaying for the presence or absence of a SAPPA staining pattern by detecting the presence or absence of the second complex, where a low level of ANCA-positivity indicated by a low level of the first complex and the presence of a SAPPA staining pattern indicate the presence of SAPPA, provided that detection of the first complex is not by histological means.

The present invention also provides a method of diagnosing a clinical subtype of Crohn's disease having a particular clinical response to anti-Th1 cytokine therapy by determining the presence of SAPPA in a patient with CD by obtaining a serum sample from the patient with CD, determining by non-histological means the level of ANCA-positivity in patient sera diluted at least about 100-fold, and assaying for the presence or absence of a SAPPA staining pattern, where low level ANCA-positivity in patient sera diluted at least about 100-fold and the presence of a SAPPA staining pattern indicate the presence of SAPPA, provided that the detection of ANCA is not by histological means.

As used herein, the term "complex" is synonymous with "immune complex" and means an aggregate of two or more molecules that results from specific binding between an antigen, such as a protein or peptide, and an antibody. For example, a complex can be formed by specific binding of neutrophil and ANCA.

As used herein, the term "antigen specific for ANCA" is an antigen or mixture of antigens that is bound specifically by anti-neutrophil cytoplasmic antibody. For example, neutrophil is a particularly useful antigen specific for ANCA that can be obtained from a variety of sources, such as from blood derived from a human, non-human primate, rabbit, rat or mouse. Methods for preparing neutrophil are well known in the art; for example, human neutrophil can be prepared from human peripheral blood using sedimentation in 1% dextran as described in Saxon et al., supra, 1990. Preferably, neutrophil employed in the assay will have specific reactivity with the species from which the serum sample is obtained. For example, in an assay for ANCA from a human patient, a human neutrophil is preferably employed. In addition, an antigen purified from neutrophil, which is bound specifically by ANCA, also can be an antigen specific for ANCA useful in the present invention.

The present invention also provides genetic methods of diagnosing a clinical subtype of CD having an inferior clinical response to anti-Th1 cytokine therapy. As set forth in Example II and summarized in Table 8, the presence of either of the TNF microsatellite haplotypes a10b4c1d3e3 or a11b4c1d3e3 is diagnostic of a clinical subtype of CD having an inferior clinical response to anti-Th1 cytokine therapy. While the percentage of cA2-treated CD patients going into remission in the unstratified population was 25%, clinical subtypes characterized by the presence a10b4c1d3e3 or a11b4c1d3e3 had significantly reduced remission rates of only about 5% or 14%, respectively. These results indicate that the presence of a10b4c1d3e3 or a11b4c1d3e3 predicts poor responsiveness to anti-Th1 cytokine therapy.

Thus, the invention provides a method of diagnosing a clinical subtype of CD having an inferior clinical response to anti-Th1 cytokine therapy by determining the presence or absence of a TNF microsatellite allele selected from the group consisting of TNFa10, TNFb4, TNFc1, TNFd3 and TNFe3 in a patient with CD, where the presence of at least one of these TNF microsatellite alleles indicates a clinical subtype of CD having an inferior clinical response to anti-Th1 cytokine therapy.

The present invention also provides a method of diagnosing a clinical subtype of CD having an inferior clinical response to anti-Th1 cytokine therapy by determining the presence or absence of at least two TNF microsatellite alleles selected from the group consisting of TNFa10, TNFb4, TNFc1, TNFd3 and TNFe3 in a patient with CD, where the presence of an allelic combination including at least two of said alleles indicates a clinical subtype of CD having an inferior clinical response to anti-Th1 cytokine therapy. The allelic combination can include three alleles such as TNFa10, TNFb4 and TNFc1. The allelic combination also can include four alleles such as TNFa10, TNFb4, TNFc1 and TNFd3, or such as TNFa10, TNFb4, TNFc1 and TNFe3. In addition, the allelic combination can include TNFa10, TNFb4, TNFc1, TNFd3 and TNFe3.

The invention further provides a method of diagnosing a clinical subtype of CD having an inferior clinical response to anti-Th1 cytokine therapy by determining the presence or absence of a TNF microsatellite allele selected from the group consisting of TNFa11, TNFb4, TNFc1, TNFd3 and TNFe3 in a patient with CD, where the presence of at least one of these TNF microsatellite alleles indicates a clinical subtype of CD having an inferior clinical response to anti-Th1 cytokine therapy.

In addition, the invention provides a method of diagnosing a clinical subtype of CD having an inferior clinical response to anti-Th1 cytokine therapy by determining the presence or absence of at least two TNF microsatellite alleles selected from the group consisting of TNFa11, TNFb4, TNFc1, TNFd3 and TNFe3 in a patient with CD, where the presence of an allelic combination including at least two of said alleles indicates a clinical subtype of CD having an inferior clinical response to anti-Th1 cytokine therapy. The allelic combination can include three alleles such as TNFa11, TNFb4 and TNFc1. The allelic combination also can include four alleles such as TNFa11, TNFb4, TNFc1 and TNFd3, or such as TNFa11, TNFb4, TNFc1 and TNFe3. In addition, the allelic combination can include TNFa11, TNFb4, TNFc1, TNFd3 and TNFe3.

The human genome contains a large number of interspersed simple tandem repeat sequences, designated microsatellites, which vary in length among individuals and therefore serve as highly informative polymorphic markers. Although the function of these regions is unknown, there are 50,000 to 100,000 microsatellite sequence repeats throughout the human genome. This abundant class of DNA polymorphisms can be typed, for example, using the polymerase chain reaction (PCR), as described further below. In particular, five polymorphic TNF microsatellite loci, denoted TNFa, TNFb, TNFc, TNFd and TNFe, have been described in association with the TNF-$\alpha$ and TNF-$\beta$ genes.

The TNF microsatellite a10b4c1d3e3 and a11b4c1d3e3 haplotypes, which are particular combination of alleles at the TNFa, TNFb, TNFc, TNFd and TNFe loci, were first identified in homozygous cell lines as described in Udalova et al., *Genomics* 16:180–186 (1993). In healthy European populations, the three-locus allelic combinations a11b4c1 and a10b4c1 are among the four most common (Crouau-Roy et al., *Human Immunol.* 38:213–216 (1993), which is incorporated herein by reference). Analysis of the five-locus a10b4c1d3e3 and a11b4c1d3e3 haplotypes in patients having inflammatory bowel disease indicated that there was no significant correlation between either of these TNF microsatellite haplotypes and the presence of Crohn's disease or ulcerative colitis (Plevy et al., *Gastroenterol.* 110:1053–1060 (1996), which is incorporated herein by reference). Thus, prior to the present invention, the existence of the a10b4c1d3e3 and a11b4c1d3e3 TNF microsatellite haplotypes was known but there was no knowledge of the utility of these haplotypes in the diagnosis of clinical subtypes of Crohn's disease.

As used herein, the term "microsatellite allele" means a nucleotide sequence that is distinguished by its number of nucleotide or dinucleotide repeats from an alternative nucleotide sequence which occupies the same chromosomal locus. As used herein, the term "TNF microsatellite allele" refers to a microsatellite allele at one of the TNFa, TNFb, TNFc, TNFd or TNFe loci.

Figure 3:
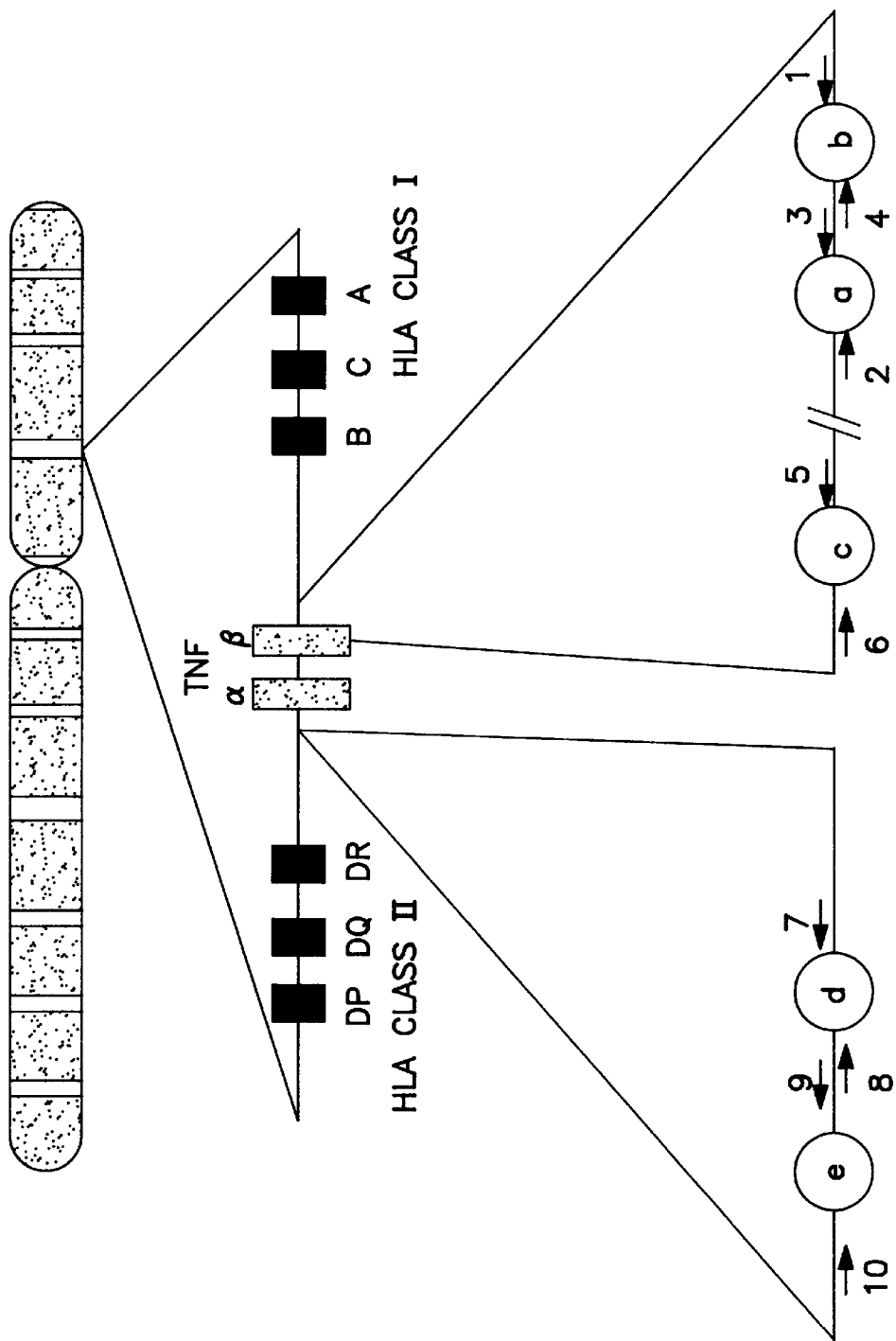
FIG. 3 shows the relative location of the five TNF microsatellite loci: TNFa, TNFb, TNFc, TNFd and TNFe. Also shown are the relative locations of oligonucleotide primers SEQ ID NOS: 1 to 10, with orientation indicated by numbered arrows.

The relative locations of the five TNF microsatellite loci are shown in FIG. 3. The TNFa and TNFb are closely linked and located 3.5 kb upstream of the TNF-β gene. TNFa microsatellites are characterized by AC/GT dinucleotide repeats, and TNFb microsatellites are characterized by TC/GA sequences that differ by 1 or 2 bases. TNF microsatellite c, which is located within the intron of the TNF-β gene, is characterized by TC/GA dinucleotide sequence repeats. TNFd and TNFe are located 8 to 10 kb downstream of the TNF-α gene. TNFd is characterized by TC/GA-like sequence repeats, which are similar to TC/GA repeats except that the repeats are interrupted by an extra base pair. TNFe is characterized by TC/GA dinucleotide sequence repeats. These TNF microsatellite loci have been described in Nedospasov et al., *J. Immunol.* 147:1053–1059 (1991), Jongeneel et al., *Proc. Natl. Acad. Sci.* USA 88:9717–9721 (1991) and Udalova et al., supra, 1993, each of which is incorporated herein by reference.

As used herein, the term "allelic combination" means a particular combination of alleles at two or more TNF microsatellite loci. An allelic combination can involve particular alleles at two, three, four or five TNF microsatellite loci.

As used herein, the term "TNF microsatellite haplotype" means a five-locus allelic combination defined by particular alleles at the TNFa, TNFb, TNFc, TNFd and TNFe loci. The term "TNFa10b4c1d3e3 haplotype" is synonymous with "a10b4c1d3e3 haplotype" and means a TNF microsatellite haplotype defined by the combination of the TNFa10 allele, TNFb4 allele, TNFc1 allele, TNFd3 allele and TNFe3 allele. A patient who is "a10b4c1d3e3-positive" has the a10b4c1d3e3 haplotype.

Similarly, the term "TNFa11b4c1d3e3 haplotype" is synonymous with "a11b4c1d3e3 haplotype" and means a TNF microsatellite haplotype defined by the combination of the TNFa11 allele, TNFb4 allele, TNFc1 allele, TNFd3 allele and TNFe3 allele. A patient who is "a11b4c1d3e3-positive" has the a11b4c1d3e3 haplotype.

Similarly, the term "TNFa2b1c2d4e1 haplotype" is synonymous with "a2b1c2d4e1 haplotype" and means a TNF microsatellite haplotype defined by the combination of the TNFa2 allele, TNFb1 allele, TNFc2 allele, TNFd4 allele and TNFe1 allele. A patient who is "a2b1c2d4e1-positive" has the a2b1c2d4e1 haplotype.

The presence or absence of a TNF microsatellite allele can be determined using a variety of methods well known in the art. Such methods are based on the unique length or nucleotide sequence of a particular microsatellite allele, where the unique length or nucleotide sequence distinguish that allele from other alleles at the same locus. For example, TNF microsatellite alleles of a single locus can be distinguished based on the size of an amplified product prepared with flanking primers relative to amplification of nucleic acid having a known TNF microsatellite allele (see Example IV, see, also, Udalova et al., supra, 1993). Microsatellite alleles differ by one dinucleotide repeat for TNFa, TNFc, TNFd, and TNFe. For TNFb, alleles differ by 1 or 2 bases as reported in Udalova et al., supra, 1993. Sequence analysis, including automated sequence analysis, also can be useful in determining whether a particular TNF microsatellite allele is present, as described further below. In addition, assays such as allele-specific oligonucleotide hybridization can be used to determine whether a particular TNF microsatellite allele is present (see Mullis et al. (ed.), *The Polymerase Chain Reaction* Boston: Birkhäuser (1994), which is incorporated herein by reference). Well known electrophoretic methods such as denaturing gradient gel electrophoresis also are useful in the methods of the invention (see, for example, Innis et al., *PCR Protocols: A Guide to Methods and Application,* San Diego: Academic Press, Inc. (1990), which is incorporated herein by reference).

Also provided by the present invention, in a method of treating a patient with Crohn's disease with anti-Th1 cytokine therapy, is an improvement including determining the presence or absence of a TNFa10b4c1d3e3 haplotype in the patient with CD, where the presence of the TNFa10b4c1d3e3 haplotype indicates a clinical subtype of CD having an inferior clinical response to anti-Th1 cytokine therapy.

The present invention also provides a method of diagnosing a clinical subtype of CD having an inferior clinical response to anti-Th1 cytokine therapy by determining the presence or absence of a TNFa10b4c1d3e3 haplotype in a patient with CD, where the presence of the TNFa10b4c1d3e3 haplotype indicates a clinical subtype of CD having an inferior clinical response to anti-Th1 cytokine therapy.

The invention also provides, in a method of treating a patient with Crohn's disease with anti-Th1 cytokine therapy, an improvement including determining the presence or absence of a TNFa11b4c1d3e3 haplotype in the patient with CD, where the presence of the TNFa11b4c1d3e3 haplotype indicates a clinical subtype of CD having an inferior clinical response to anti-Th1 cytokine therapy.

The present invention also provides a method of diagnosing a clinical subtype of CD having an inferior clinical response to anti-Th1 cytokine therapy by determining the presence or absence of a TNFa11b4c1d3e3 haplotype in a patient with CD, where the presence of the TNFa11b4c1d3e3 haplotype indicates a clinical subtype of CD having an inferior clinical response to anti-Th1 cytokine therapy.

The present invention further provides a method of diagnosing a clinical subtype of CD having an inferior clinical response to anti-Th1 cytokine therapy by determining the presence or absence of a TNFa10b4c1d3e3 haplotype and determining the presence or absence of a TNFa11b4c1d3e3 haplotype, where the presence of the TNFa10b4c1d3e3 haplotype indicates a clinical subtype of CD having an inferior clinical response to anti-Th1 cytokine therapy and the presence of the TNFa11b4c1d3e3 haplotype independently indicates a clinical subtype of CD having an inferior clinical response to anti-Th1 cytokine therapy.

As described herein, the TNFa10b4c1d3e3 haplotype or TNFa11b4c1d3e3 haplotype each is independently diagnostic of a clinical subtype of Crohn's disease having an inferior clinical response to anti-Th1 cytokine therapy. The term "independently," when used herein in reference to the presence of a genetic or serological marker useful in a method of the invention, means that the genetic or serological marker, alone, is diagnostic of the recited clinical subtype of Crohn's disease. Thus, for example, a patient who is TNFa10b4c1d3e3-positive and TNFa11b4c1d3e3-negative has the clinical subtype of CD with an inferior clinical response to anti-Th1 cytokine therapy.

The present invention provides a method of diagnosing a clinical subtype of CD having an inferior clinical response to anti-Th1 cytokine therapy by determining the presence or absence of a TNFa10b4c1d3e3 haplotype, where the presence or absence of the haplotype is determined by obtaining material having nucleic acid including TNFa, TNFb, TNFc, TNFd and TNFe loci from the patient; enzymatically amplifying the nucleic acid using pairs of oligonucleotide primers complementary to nucleotide sequences flanking each of the TNFa, TNFb, TNFc, TNFd and TNFe loci to produce amplified products including TNFa, TNFb, TNFc, TNFd or TNFe; and electrophoresing the amplified products to identify the TNFa10b4c1d3e3 haplotype, where the presence of the TNFa10b4c1d3e3 haplotype indicates a clinical subtype of CD having an inferior clinical response to anti-Th1 cytokine therapy.

The present invention also provides a method of diagnosing a clinical subtype of CD having an inferior clinical response to anti-Th1 cytokine therapy by determining the presence or absence of a TNFa11b4c1d3e3 haplotype, where the presence or absence of the haplotype is determined by obtaining material having nucleic acid including TNFa, TNFb, TNFc, TNFd and TNFe loci from the patient; enzymatically amplifying the nucleic acid using pairs of oligonucleotide primers complementary to nucleotide sequences flanking each of the TNFa, TNFb, TNFc, TNFd and TNFe loci to produce amplified products including TNFa, TNFb, TNFc, TNFd or TNFe; and electrophoresing the amplified products to identify the TNFa11b4c1d3e3 haplotype, where the presence of the TNFa11b4c1d3e3 haplotype indicates a clinical subtype of CD having an inferior clinical response to anti-Th1 cytokine therapy.

As used herein, the term "material" means any biological matter from which nucleic acid can be prepared. For example, the term material encompasses whole blood, plasma or other bodily fluid or tissue that contains nucleic acid. A preferred material is patient sera, which can be obtained readily by non-invasive means and used to prepare genomic DNA for the diagnosis of a clinical subtype of Crohn's disease according to the methods of the invention.

As used herein, the term "nucleic acid" means a polynucleotide such as deoxyribonucleic acid (DNA). A nucleic acid can be either single-stranded or double-stranded. One skilled in the art can practice the methods of the invention with a nucleic acid such as genomic DNA.

The term "enzymatically amplifying," as used herein in reference to a nucleic acid including one or more of the five TNF microsatellite loci, means an enzymatic process whereby, from an initial amount of nucleic acid including or more of the five TNF microsatellite loci, a larger amount of nucleic acid containing some or all of the same nucleic acid sequence is produced. The polymerase chain reaction (PCR), which involves the use of a thermo-stable DNA polymerase and repeated cycles of polymerization, is particularly useful in the methods of the invention. PCR is well known in the art as described, for example in Mullis et al., supra, 1994, and Innis et al., supra, 1990. As used herein, the term "amplified product" means nucleic acid produced by the process of enzymatic amplification.

The term "oligonucleotide primers complementary to nucleotide sequences flanking each of the TNFa, TNFb, TNFc, TNFd and TNFe loci," as used herein, means linear oligonucleotides of about ten to about fifty nucleotides in length that are complementary to nucleotide sequences 5' or 3' of a TNF locus to be amplified. One can use, for example, a pair of oligonucleotide primers in which one of the primers is complementary to a nucleotide sequence 5' of the TNF microsatellite locus or loci to be amplified while the other primer of the pair is complementary to a nucleotide sequence located 3' of the TNF microsatellite locus or loci to be amplified. One skilled in the art understands that a pair of oligonucleotide primers means two oligonucleotides complementary to opposite strands of nucleic acid and flanking the locus to be amplified.

Primers suitable for use in amplifying nucleic acid including TNF microsatellite loci TNFa, TNFb, TNFc, TNFd or TNFe can be generated according to the sequences described herein or using the map and sequence of the TNF locus available from Genbank as part of the human genome project funded through the National Institute of Health and incorporated herein by reference. The map and sequence of the TNF locus can be readily obtained for example, on the internet world wide web at http://www.ncbi.nlm.nih.gov. NCBI's database is incorporated herein in its entirety. Primers useful in the methods of the invention can have, for example, a length of about 12, 15, 17, 20 or 25 nucleotides. Exemplary oligonucleotide primers complementary to nucleotide sequences flanking the five TNF loci are described further below.

For use in the methods of the invention, one skilled in the art understands that an oligonucleotide primer complementary to a nucleotide sequence flanking a TNF locus is relatively specific for amplification of nucleic acid including the TNF microsatellite locus to be amplified. For example, when the presence of a particular TNF microsatellite allele is to be determined by sequence analysis, an oligonucleotide primer preferably is complementary only to a nucleotide sequence flanking the TNF locus to be amplified. However, when the presence of a particular TNF microsatellite allele is determined based on the size of the amplified product, an oligonucleotide primer can be complementary to other unrelated sequences in addition to the nucleotide sequence flanking the TNF locus to be amplified. In this case, one or more amplified products unrelated to the TNF locus may be produced in addition to the amplified product of interest. However, for such a primer to be useful, one skilled in the art understands that the size of the one or more unrelated amplified products must be distinct from the size of the amplified product including the TNF locus.

FIG. 3 shows the relative location and orientation of oligonucleotide primers complementary to nucleotide sequences flanking TNFa, TNFb, TNFc, TNFd and TNFe with regard to TNF microsatellite loci. Table 9 shows the primer sequences. Oligonucleotide primers complementary to a nucleotide sequence flanking TNFa and TNFb are SEQ ID NOS: 1 and 2. These oligonucleotide primers can be used together as a pair or in combination with another suitable oligonucleotide primer to amplify genomic DNA including TNFa and TNFb. SEQ ID NO: 1 is complementary to a nucleotide sequence 5' of TNFb, and SEQ ID NO: 2 is complementary to a nucleotide sequence 3' of TNFa. If desired, nucleic acid including the TNFa locus can be individually amplified without amplifying TNFb. For example, SEQ ID NOS: 2 and 3 can be used as a primer pair for amplification of the TNFa locus. Similarly, one can amplify nucleic acid including the TNFb locus without amplifying the TNFa locus.

SEQ ID NOS: 5 and 6 are oligonucleotide primers that can be used to amplify genomic DNA that includes TNFc. Primers SEQ ID NOS: 5 and 6 can be used as a pair or each in combination with another suitable primer. As depicted in FIG. 3, SEQ ID NO: 5 is complementary to a nucleotide sequence located 5' of the TNFc locus, and SEQ ID NO: 6 is complementary to a nucleotide sequence located 3' of the TNFc locus.

Primers SEQ ID NO: 7 and 10 are suitable for use in amplifying genomic DNA including TNFd and TNFe and can be used as a pair or each in combination with another suitable primer. SEQ ID NO: 7 is complementary to a nucleotide sequence 5' of TNFd, as depicted in FIG. 3, and SEQ ID NO: 10 is complementary to a nucleotide sequence 3' of TNFe. One also can amplify nucleic acid encoding the alleles of TNFd or TNFe separately: for example, SEQ ID NOS: 7 and 8 can be used as a primer pair to amplify nucleic acid including TNFd alleles, and SEQ ID NO: 9 and 10 can be used as a primer pair to amplify nucleic acid including TNFe alleles. FIG. 3 depicts the relative location and orientation of these primers in relation to TNF microsatellite loci.

TNF microsatellite a (TNFa) has at least thirteen alleles designated TNFa1 through TNFa13. Each of the TNFa alleles, which are characterized by a particular number of AC/GT dinucleotide sequence repeats, have a characteristic size when amplified by a particular pair of flanking primers. For each TNFa allele, the size of the amplified nucleic acid product generated with primers SEQ ID NO: 2 and SEQ ID NO: 3 is shown in Table 1.

TNF microsatellite b (TNFb) has at least seven alleles designated TNFb1 through TNFb7. Each of these alleles has a characteristic number of TC/GA dinucleotide sequence repeats ranging from 8 to 20 repeats and a characteristic size when amplified with a particular pair of flanking primers. Table 2 indicates the name, type of sequence repeat and size of each TNFb allele produced by flanking primers SEQ ID NO: 1 and SEQ ID NO: 4.

TNF microsatellite c (TNFc) has at least two alleles, which are designated TNFc1 and TNFc2. When amplified with flanking primers SEQ ID NO: 5 and SEQ ID NO: 6, TNFc1, which is characterized by a series of nine TC/GA dinucleotide sequence repeats, is 160 base pairs in size. TNFc2, which is characterized by a series often TC/GA dinucleotide sequence repeats, is 162 base pairs in size when amplified with primers SEQ ID NO: 5 and SEQ ID NO: 6.

The TNF microsatellite d locus (TNFd) has at least seven alleles designated TNFd1 through TNFd7. Each of the TNF microsatellite d alleles has a characteristic size when amplified with primers SEQ ID NO: 7 and SEQ ID NO: 8 as shown in Table 3.

The TNF microsatellite e locus (TNFe) has at least four alleles denoted TNFe1 through TNFe4. TNFe1 is 99 base pairs in size and is further characterized by a series of TC/GA sequence repeats. TNFe2 is 101 base pairs in size and is further characterized by a series of TC/GA sequence repeats. TNFe3 is 103 base pairs in size and is characterized by a series of TC/GA sequence repeats. TNFe4, which has not yet been identified in humans, is 105 base pairs in size and characterized by a series of TC/GA sequence repeats.

TABLE 1

Characterization of TNFa alleles
with primers SEQ ID NO: 2 and SEQ ID NO: 3

| Allele | Repeat Sequence | Number of Repeats | Size (bp) |
| --- | --- | --- | --- |
| TNFa1 | AC/GT | 6 | 98 |
| TNFa2 | AC/GT | 7 | 100 |
| TNFa3 | AC/GT | 8 | 102 |
| TNFa4 | AC/GT | 9 | 104 |
| TNFa5 | AC/GT | 10 | 106 |
| TNFa6 | AC/GT | 11 | 108 |
| TNFa7 | AC/GT | 12 | 110 |
| TNFa8 | AC/GT | 13 | 112 |
| TNFa9 | AC/GT | 14 | 114 |
| TNFa10 | AC/GT | 15 | 116 |
| TNFa11 | AC/GT | 16 | 118 |
| TNFa12 | AC/GT | 17 | 120 |
| TNFa13 | AC/GT | 18 | 122 |

One skilled in the art understands the importance of determining an allele unambiguously by comparison to a positive control. It is well known that particular alleles can migrate with an anomalous molecular weight. For example, TNFc1 and TNFc2, which are 160 and 162 bp in size, respectively, can migrate as fragments of 161.5 bp and 163.5 bp, respectively, when analyzed on an automated sequencer such as Applied Biosystem's 373 DNA Sequencer. Similarly, the seven TNFd alleles, which are reported to be 124 bp to 136 bp in size, can have apparent molecular weights of 126 bp to 138 bp when analyzed on the 373 DNA Sequencer, for example.

TABLE 2

Characterization of TNFb alleles
with primers SEQ ID NO: 1 and SEQ ID NO: 4

| Allele | Repeat Sequence | Size (bp) |
| --- | --- | --- |
| TNFb1 | TC/GA | 127 |
| TNFb2 | TC/GA | 128 |
| TNFb3 | TC/GA | 129 |
| TNFb4 | TC/GA | 130 |
| TNFb5 | TC/GA | 131 |
| TNFb6 | TC/GA | 132 |
| TNFb7 | TC/GA | 133 |

Positive controls for TNF microsatellite haplotypes a10b4c1d3e3 and a11b4c1d3e3 can be useful in determining whether these haplotypes are present in a patient with CD. A convenient positive control can be a cell line known to have the TNF microsatellite haplotype of interest, such as those described in Udalova et al., supra, 1993. A positive control for the presence of the a10b4c1d3e3 haplotype can be, for example, cell line D0208915, BM16, 1227ABO, BM14, BM92, RML, TEM, WDV, YAR, PLH or KAS-011 or

TABLE 3

Characterization of TNFd alleles
with primers SEQ ID NO: 7 and SEQ ID NO: 8

| Allele | Repeat Sequence | Size (bp) |
| --- | --- | --- |
| TNFd1 | TC/GA-like | 124 |
| TNFd2 | TC/GA-like | 126 |
| TNFd3 | TC/GA-like | 128 |
| TNFd4 | TC/GA-like | 130 |
| TNFd5 | TC/GA-like | 132 |
| TNFd6 | TC/GA-like | 134 |
| TNFd7 | TC/GA-like | 136 | another cell line known to have the a10b4c1d3e3 haplotype (see Table 4). These cell lines are readily available from the American Society of Histocompatibility and Immunogenetics Workshop (ASHI) or the Center for Human Polymorphism Studies (CEPH).

A positive control for the presence of the a11b4c1d3e3 haplotype can be cell line MGAR, SCHU, LD28, HO 104, ST8, SAVC, HHK, SA, HHKB, LKT3 or another cell line known to have the a11b4c1d3e3 haplotype as described, for example, in Udalova, supra, 1993. These cell lines are available from the ASHI or CEPH using the accession numbers shown in Table 5.

TABLE 4

Positive controls for the a10b4c1d3e3 haplotype

| Cell line | ASHI accession number | CEPH accession number |
| --- | --- | --- |
| D0208915 | 9008 | ws58 |
| BM16 | 9038 | ws57 |

TABLE 4-continued

Positive controls for the a10b4c1d3e3 haplotype

| Cell line | ASHI accession number | CEPH accession number |
|---|---|---|
| 31227ABO | 9061 | ws55 |
| BM14 | 9033 | ws08 |
| BM92 | 9092 | ws50 |
| RML | 9016 | ws43 |
| TEM | 9057 | ws38 |
| WDV | 9062 | ws47 |
| YAR | 9026 | ws63 |
| PLH | 9047 | ws22 |
| KAS-011 | 9009 | ws49 |

The present invention also provides a method of diagnosing a clinical subtype of CD having an inferior clinical response to anti-Th1 cytokine therapy by determining the presence or absence of a TNFa10b4c1d3e3 haplotype by obtaining material having nucleic acid including TNFa, TNFb, TNFc, TNFd and TNFe loci from the patient; enzymatically amplifying the nucleic acid using pairs of oligonucleotide primers complementary to nucleotide sequences flanking each of the TNFa, TNFb, TNFc, TNFd and TNFe loci to produce amplified products including TNFa, TNFb, TNFc, TNFd or TNFe; and sequencing the amplified products to identify the TNFa10b4c1d3e3 haplotype, where the presence of the TNFa10b4c1d3e3 haplotype indicates a clinical subtype of CD having an inferior clinical response to anti-Th1 cytokine therapy.

TABLE 5

Positive controls for the a11b4c1d3e3 haplotype

| Cell line | ASHI accession number | CEPH accession number |
|---|---|---|
| MGAR | 9014 | ws02 |
| SCHU | 9013 | ws07 |
| LD28 | 9083 | — |
| HO 104 | 9082 | ws66 |
| WT8 | 9017 | ws05 |
| SAVC | 9034 | ws52 |
| HHK | — | ws45 |
| SA | 9001 | — |
| HHKB | 9065 | — |
| LKT3 | 9017 | ws04 |

The present invention also provides a method of diagnosing a clinical subtype of CD having an inferior clinical response to anti-Th1 cytokine therapy by determining the presence or absence of a TNFa11b4c1d3e3 haplotype by obtaining material having nucleic acid including TNFa, TNFb, TNFc, TNFd and TNFe loci from the patient; enzymatically amplifying the nucleic acid using pairs of oligonucleotide primers complementary to nucleotide sequences flanking each of the TNFa, TNFb, TNFc, TNFd and TNFe loci to produce amplified products including TNFa, TNFb, TNFc, TNFd or TNFe; and sequencing the amplified products to identify the TNFa11b4c1d3e3 haplotype, where the presence of the TNFa11b4c1d3e3 haplotype indicates a clinical sub type of CD having an inferior clinical response to anti-Th1 cytokine therapy.

The term "sequencing," as used herein, means a process for determining the order of nucleotides in a nucleic acid. A variety of methods for sequencing nucleic acids are well known in the art. Such sequencing methods include the Sanger method of dideoxy-mediated chain termination as described, for example, in Sanger et al., Proc. Natl. Acad. Sci. 74:5463 (1977), which is incorporated herein by reference (see, also, "DNA Sequencing" in Sambrook et al. (eds.), Molecular Cloning: A Laboratory Manual (Second Edition), Plainview, N.Y.: Cold Spring Harbor Laboratory Press (1989), which is incorporated herein by reference). A variety of polymerases including the Klenow fragment of E. coli DNA polymerase I; Sequenase™ (T7 DNA polymerase); Taq DNA polymerase and Amplitaq can be used in enzymatic sequencing methods. Well known sequencing methods also include Maxam-Gilber chemical degradation of DNA (see Maxam and Gilbert, Methods Enzymol. 65:499 (1980), which is incorporated herein by reference, and "DNA Sequencing" in Sambrook et al., supra, 1989).

One skilled in the art understands that an amplified product can be sequenced directly or subcloned into a vector prior to sequence analysis. Commercially available sequencing kits including the Sequenase™ kit from Amersham Life Science (Arlington Heights, Ill.) can be used to sequence an amplified product in the methods of the invention. Automated sequence analysis also can be useful, and automated sequencing instruments such as the Prism 377 DNA Sequencer or the 373 DNA Sequencer are commercially available, for example, from Applied Biosystems (Foster City, Calif.; see, also, Frazier et al., Electrophoresis 17:1550–1552 (1996), which is incorporated herein by reference).

The invention further provides a method of diagnosing a clinical subtype of CD having a sustained superior clinical response to anti-Th1 cytokine therapy by determining the presence or absence of a TNF microsatellite allele selected from the group consisting of TNFa2, TNFb1, TNFc2, TNFd4 and TNFe1 in a patient with CD, where the presence of at least one of these TNF microsatellite alleles indicates a clinical subtype of CD having a sustained superior clinical response to anti-Th1 cytokine therapy.

In addition, the invention provides a method of diagnosing a clinical subtype of CD having a sustained superior clinical response to anti-Th1 cytokine therapy by determining the presence or absence of at least two TNF microsatellite alleles selected from the group consisting of TNFa2, TNFb1, TNFc2, TNFd4 and TNFe1 in a patient with CD, where the presence of an allelic combination including at least two of said alleles indicates a clinical subtype of CD having a sustained superior clinical response to anti-Th1 cytokine therapy. The allelic combination can include three alleles such as TNFa2, TNFb1 and TNFc2. The allelic combination also can include four alleles such as TNFa2, TNFb1, TNFc2 and TNFd4, or such as TNFa2, TNFb1, TNFc2 and TNFe1. In addition, the allelic combination can include TNFa2, TNFb1, TNFc2, TNFd4 and TNFe1.

Further provided herein is a method of determining a clinical subtype of CD having a sustained superior clinical response to anti-Th1 cytokine therapy by determining the presence or absence of a TNFa2b1c2d4e1 haplotype in a patient with CD, where the presence of the TNFa2b1c2d4e1 haplotype indicates a clinical subtype having a sustained superior clinical response to anti-Th1 cytokine therapy.

Figure 6A:
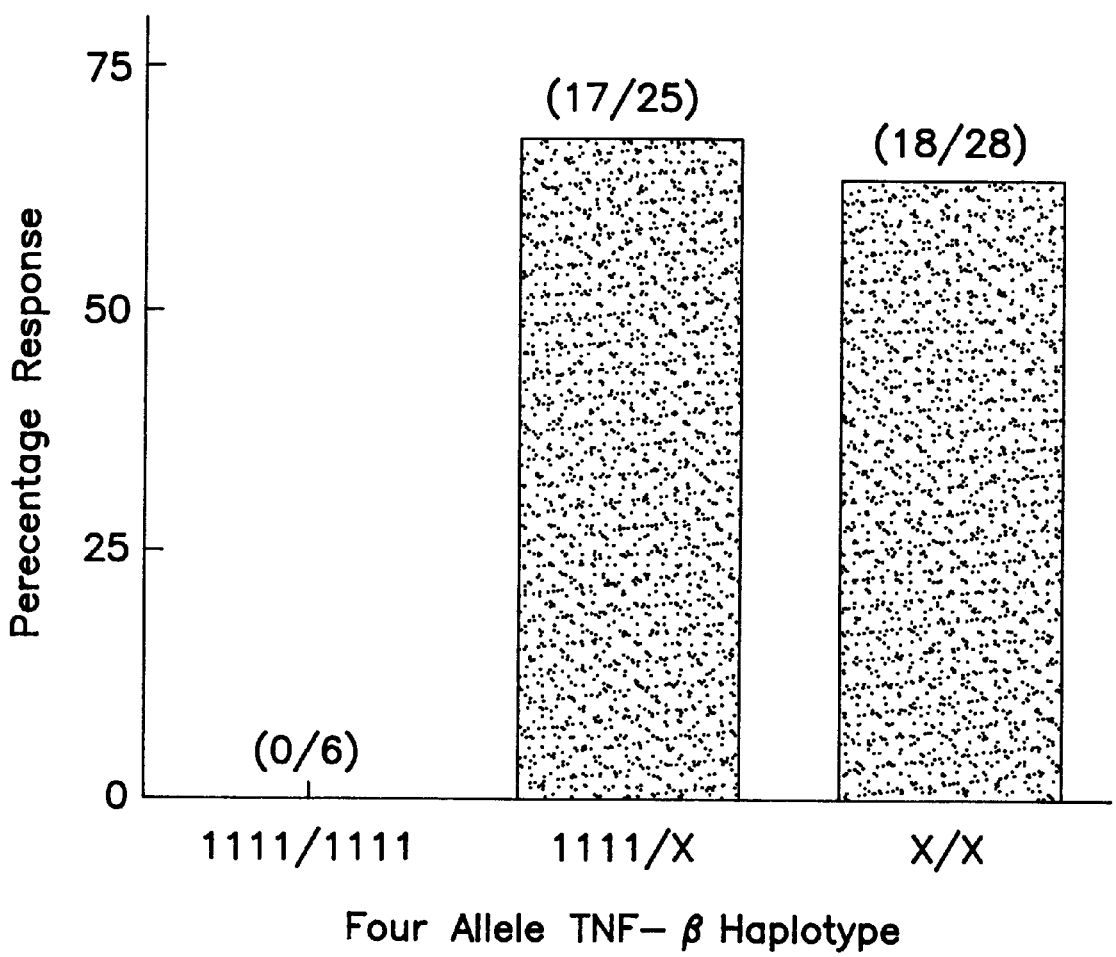
FIGS. 6A–C shows the response and ANCA status of CD patients subtyped according to the TNF-β four locus haplotype.

The invention also provides methods relating to a novel four locus TNF-β haplotype involving the TNFc, aa13L, aa26 and NcoI loci. The TNF-β "1111 haplotype" denotes that the more common of the two alleles is present at each of the biallelic TNFc, aa13L, aa26 and NcoI loci. As shown in FIG. 6A, the presence of the homozygous 1111/1111 TNF-β four locus haplotype correlated with a lack of clinical response to cA2 in six of six patients. In contrast, approximately 60% of patients heterozygous ("1111/X") or lacking the 1111 haplotype ("X/X") had a clinical response to cA2 therapy. These results indicate that the presence of a homozygous TNF-β 1111 haplotype is diagnostic of an inferior clinical response to anti-Th1 cytokine therapy.

Thus, there is provided a method of diagnosing a clinical subtype of CD having an inferior clinical response to anti-Th1 cytokine therapy by determining the presence or absence of a homozygous TNF-β 1111 haplotype at the TNFc, aa13L, aa26 and NcoI loci in a patient with CD, where the presence of the homozygous TNF-β 1111 haplotype indicates a clinical subtype of CD having an inferior clinical response to anti-Th1 cytokine therapy.

As used herein, the term "TNF-β four locus haplotype" means a four-locus allelic combination defined by particular alleles at the biallelic TNFc, aa13L, aa26 and NcoI loci. The term "TNF-β 1111 haplotype" is synonymous with "1111 haplotype" and means a TNF-β four locus haplotype defined by the combination of the more common of the two alleles at TNFc, the more common of the two alleles at aa13L, the more common of the two alleles at aa26 and the more common of the two alleles at the NcoI locus. An individual may be homozygous or heterozygous for the 1111 haplotype. An individual homozygous for the 1111 haplotype is an individual having two copies of the 1111 haplotype.

The term "common allele," as used herein in reference to an allele at a biallelic locus, is synonymous with the term "1" allele. Similarly, the term "rare allele" is synonymous with "2" allele. The common and rare alleles at the TNFc, aa13L, aa26 and NcoI loci are described further below.

Described herein are methods for determining whether the common or rare allele is present at each of the biallelic TNFc, aa13L, aa26 and NcoI loci. The genomic sequence including this region, designated HUMTNFAB, is available from GenBank under accession number M16441. The TNF-β cDNA sequence, designated HUMLTNFB, is available from GenBank under accession number D12614.

The common or "1" allele at the TNFc locus, denoted TNFc 1, is characterized by a series of nine TC/GA dinucleotide sequence repeats. The rare or "2" allele, denoted TNFc2, is characterized by a series of ten TC/GA dinucleotide sequence repeats. Methods for determining whether the allele at the TNFc locus is c1 or c2 are described in Udalova, supra, 1993, and in Example IV.

The aa13L polymorphism is present at amino acid 13 of the TNF-β leader sequence. The common or "1" aa13L allele has a "T" at position 207 of the TNF-β cDNA sequence shown in FIG. 4B; the codon corresponding to the "1" allele encodes a cysteine. The rare or "2" aa13L allele has a "C" at position 207 of the TNF-β cDNA sequence shown in FIG. 4B; the codon corresponding to the "2" allele encodes an arginine. The common aa13L allele is in linkage association with the common TNFc allele described above. Methods for determining whether the common or rare allele is present at aa13L include allele-specific oligonucleotide hybridization as described in Example V. Provided herein is the allele-specific oligonucleotide SEQ ID NO: 15 for determining the presence of the aa13L "1" allele and the allele-specific oligonucleotide SEQ ID NO: 16 for determining the presence of the aa13L "2" allele.

The aa26 polymorphism present at amino acid 26 of mature TNF-β has been previously described (Messer et al., J. Exp. Med. 173:209–219 (1991), which is incorporated herein by reference). The common or "1" aa26 allele has a "C" at position 349 of the TNF-β nucleotide sequence shown in FIG. 4B; the codon corresponding to the "1" allele at aa26 encodes threonine. The rare or "2" aa26 allele has an "A" at position 349 of the TNF-β nucleotide sequence shown in FIG. 4B; the codon corresponding to the "2" allele encodes asparagine. Methods for determining the allele at the aa26 locus include allele-specific oligonucleotide hybridization as described in Example V. Provided herein is the allele-specific oligonucleotide SEQ ID NO: 17 for determining the presence of the aa26 "1" allele and the allele-specific oligonucleotide SEQ ID NO: 18 for determining the presence of the aa26 "2" allele.

The NcoI restriction fragment length polymorphism in the first intron of TNF-β also has been previously described (Webb and Chaplin, J. Immunol. 145: 1278–1285 (1990), which is incorporated herein by reference). Southern analysis has shown that a 10.5 kb NcoI fragment is most common, with a 5.4 TNF-β NcoI fragment present in a smaller number of individuals. The NcoI site is absent in the common or "1" allele, while the NcoI site is present in the the rare or "2" allele. The rare NcoI allele is in linkage association with the rare aa26 allele described above (Messing et al., supra, 1991). Methods for determining the allele at the NcoI locus are described in Webb and Chaplin, supra, 1990, and in Example V. Provided herein are primers SEQ ID NOS: 19 and 20 that can be used to amplify a fragment containing the NcoI polymorphism.

As described above, both genetic and antibody markers can be useful in determining clinical subtypes of Crohn's disease having particular responses to anti-Th1 cytokine therapy. While the antibody markers described herein can be specific for Crohn's disease, with alternate antibody markers diagnostic of clinical subtypes of other inflammatory diseases, the presence of the homozygous TNF-62 1111 haplotype disclosed herein can be used to predict an inferior clinical response to anti-Th1 cytokine therapy in a variety of diseases. In rheumatoid arthritis, multiple sclerosis and psoriasis, for example, an imbalance or Th1 and Th2 activity can play a role in the etiology of the disease. Rheumatoid arthritis, like Crohn's disease, for example, can be treated with the TNF-α neutralizing antibody cA2 (van Dulleman et al., supra, 1995). Thus, the present invention also provides a method of diagnosing a clinical subtype of rheumatoid arthritis, multiple sclerosis or psoriasis having an inferior clinical response to anti-Th1 cytokine therapy by determining the presence or absence of the homozygous TNF-β 1111 haplotype, where the presence of the homozygous TNF-β 1111 haplotype indicates the clinical subtype of rheumatoid arthritis, multiple sclerosis or psoriasis having an inferior clinical response to anti-Th1 cytokine therapy.

The invention further provides a novel TNF-β nucleotide sequence SEQ ID NO: 13, which has a polymorphism at the nucleotide corresponding to amino acid 13 of the TNF-β leader sequence. The previously described TNF-β cDNA (SEQ ID NO: 11) has a "T" at nucleotide 207 of the sequence shown in FIG. 4B. The novel TNF-β nucleotide sequence disclosed herein (SEQ ID NO: 13) differs from SEQ ID NO: 11 by the substitution of a "C" at position 207. Provided herein is a nucleic acid molecule including the nucleotide sequence of SEQ ID NO: 13 shown in FIG. 4B.

The invention also provides an allele-specific oligonucleotide primer for detection of the polymorphic TNF-β sequence SEQ ID NO: 13, which has at least 15 nucleotides of SEQ ID NO: 13 shown in FIG. 4B, including the nucleotide at position 207 of SEQ ID NO: 13. An allele-specific oligonucleotide primer for detection of the polymorphic TNF-β sequence SEQ ID NO: 13 can have, for example, about 15 to 40 nucleotides of SEQ ID NO: 13 shown in FIG. 4B, including the nucleotide at position 207. An allele-specific oligonucleotide primer for detection of the polymorphic TNF-β sequence SEQ ID NO: 13 can have, for example, a sequence of about 15, 16, 17, 18, 19, 20, 21, 22, 23, 24 or 25 nucleotides of SEQ ID NO: 13, including the nucleotide at position 207. A particularly useful allele-specific oligonucleotide primer of the invention is provided as SEQ ID NO: 16.

Also provided are related methods of determining a clinical subtype of CD having a superior clinical response to anti-Th1 cytokine therapy by determining the presence or absence of a rare allele at one of the four biallelic TNF-β loci disclosed herein. The invention provides a method of determining a clinical subtype of CD having a superior clinical response to anti-Th1 cytokine therapy by determining the presence or absence of a rare allele at the TNFc locus in a patient with CD, where the presence of the rare allele indicates a clinical subtype of CD having a superior clinical response to anti-Th1 cytokine therapy.

The invention also provides a method of determining a clinical subtype of CD having a superior clinical response to anti-Th1 cytokine therapy by determining the presence or absence of a rare allele at the aa13L locus in a patient with CD, where the presence of the rare allele indicates a clinical subtype of CD having a superior clinical response to anti-Th1 cytokine therapy.

The invention additionally provides a method of determining a clinical subtype of CD having a superior clinical response to anti-Th1 cytokine therapy by determining the presence or absence of a rare allele at the aa26 locus in a patient with CD, where the presence of the rare allele indicates a clinical subtype of CD having a superior clinical response to anti-Th1 cytokine therapy.

In addition, there is provided a method of determining a clinical subtype of CD having a superior clinical response to anti-Th1 cytokine therapy by determining the presence or absence of a rare allele at the NcoI locus in a patient with CD, where the presence of the rare allele indicates a clinical subtype of CD having a superior clinical response to anti-Th1 cytokine therapy.

The invention further provides combined serological and genetic methods of diagnosing a clinical subtype of Crohn's disease having a particular clinical response to anti-Th1 cytokine therapy. The invention provides, for example, a method of diagnosing a clinical subtype of Crohn's disease having an inferior clinical response to anti-Th1 cytokine therapy by determining whether pANCA is present in a patient with CD and determining whether the TNFa10b4c1d3e3 haplotype is present in the same patient, where the presence of pANCA indicates a clinical subtype of CD having an inferior clinical response to anti-Th1 cytokine therapy and the presence of the TNFa10b4c1d3e3 haplotype independently indicates a clinical subtype of CD having an inferior clinical response to anti-Th1 cytokine therapy.

The invention also provides a method of diagnosing a clinical subtype of Crohn's disease having an inferior clinical response to anti-Th1 cytokine therapy by determining whether pANCA is present in a patient with CD and determining whether the TNFa11b4c1d3e3 haplotype is present in the same patient, where the presence of pANCA indicates a clinical subtype of CD having an inferior clinical response to anti-Th1 cytokine therapy and the presence of the TNFa11b4c1d3e3 haplotype independently indicates a clinical subtype of CD having an inferior clinical response to anti-Th1 cytokine therapy.

The invention also provides a method of diagnosing a clinical subtype of Crohn's disease having an inferior clinical response to anti-Th1 cytokine therapy by determining whether pANCA is present in a patient with CD, determining whether the TNFa10b4c1d3e3 haplotype is present in the same patient and determining whether the TNFa11b4c1d3e3 haplotype is present in the same patient, where the presence of pANCA indicates a clinical subtype of CD having an inferior clinical response to anti-Th1 cytokine therapy, the presence of the TNFa10b4c1d3e3 haplotype independently indicates a clinical subtype of CD having an inferior clinical response to anti-Th1 cytokine therapy and the presence of the TNFa11b4c1d3e3 haplotype independently indicates a clinical subtype of CD having an inferior clinical response to anti-Th1 cytokine therapy.

In addition, there is provided herein a method of diagnosing a clinical subtype of CD having a particular clinical response to anti-Th1 cytokine therapy by determining whether SAPPA is present in a patient with CD, determining whether pANCA is present in the same patient, determining the presence or absence of a TNFa10b4c1d3e3 haplotype in the patient, determining the presence or absence of a TNFa11b4c1d3e3 haplotype in the patient and determining the presence or absence of the homozygous TNF-β 1111 haplotype at the TNFc, aa13L, aa26 and NcoI loci in the patient with CD, where the presence of SAPPA indicates a clinical subtype of CD having a superior clinical response to anti-Th1 cytokine therapy, the presence of pANCA indicates a clinical subtype of CD having an inferior clinical response to anti-Th1 cytokine therapy, the presence of the TNFa10b4c1d3e3 haplotype independently indicates a clinical subtype of CD having an inferior clinical response to anti-Th1 cytokine therapy, the presence of the TNFa11b4c1d3e3 haplotype independently indicates a clinical subtype of CD having an inferior clinical response to anti-Th1 cytokine therapy and the presence of the homozygous TNF-β 1111 haplotype in the patient with CD independently indicates a clinical subtype of CD having an inferior clinical response to anti-Th1 cytokine therapy.

The invention also provides a kit for diagnosing a clinical subtype of CD having a particular clinical response to anti-Th1 cytokine therapy, which includes neutrophil and one or more oligonucleotide primers complementary to a nucleotide sequence flanking one or more TNF microsatellite loci selected from the group consisting of TNFa, TNFb, TNFc, TNFd and TNFe.

As described above, the term oligonucleotide primer complementary to a nucleotide sequence flanking a TNF locus means a linear oligonucleotide of about ten to about fifty nucleotides in length that is complementary to a nucleotide sequence 5' or 3' of a TNF locus or loci to be amplified. Such an oligonucleotide primer can have a nucleotide sequence including, for example, the nucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10. In the kits of the invention, an oligonucleotide primer can have, for example, the nucleotide sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO:10.

A kit for diagnosing a clinical subtype of CD having a particular clinical response to anti-Th1 cytokine therapy also can include neutrophil and pairs of oligonucleotide primers complementary to nucleotide sequences flanking each of TNFa, TNFb, TNFc, TNFd and TNFe.

In a kit of the invention, the neutrophil can be alcohol-fixed neutrophil such as ethanol-fixed neutrophil or methanol-fixed neutrophil. If desired, a secondary antibody selective for ANCA also can be included in the kit. Such a secondary antibody can be anti-IgG and can be a detectable secondary antibody as described above.

The following examples are intended to illustrate but not limit the present invention.

EXAMPLE I

A Clinical Subtype of CD Poorly Responsive to Anti-Th1 Cytokine Therapy

This example demonstrates that a clinical subtype of Crohn's disease is poorly responsive to anti-TNF-α therapy.

The anti-TNF-α monoclonal antibody cA2 was used to treat patients with an established diagnosis of Crohn's disease. Treatment with the cA2 antibody induced a significant clinical response in 81%, 50% and 64% of the CD patients treated with 5 mg/kg, 10 mg/kg, or 20 mg/kg cA2, respectively, at four weeks following a single intravenous infusion. The combined clinical response among all the cA2 treatment groups was 65%, as compared to 17% in the placebo group. The clinical response was achieved early, with 61% of cA2 treated patients achieving a clinical response at the first evaluation visit at two weeks.

In addition to clinical response, the percent of CD patients achieving clinical remission, as defined by a CDAI score of less than 150, was assessed. At two weeks, 27% of cA2 treated patients achieved remission compared to 4% of the placebo group. At four weeks, 33% of the cA2 treated group had achieved remission as compared to 4% of placebo. Thus, remission was achieved in approximately one half of those patients with a clinical response at either two or four weeks.

These results demonstrate that a single infusion of anti-TNF-α monoclonal cA2 results in a clinical response in approximately 65% of Crohn's Disease patients treated with the remaining patients unresponsive to the therapy. In order to ascertain whether the non-responding CD patients represent a subgroup with disease refractory to anti-Th1 cytokine therapy such as the anti-TNF-α cA2 antibody, the non-responding patients were treated with a second infusion of 10 mg/kg cA2, and CDAI levels were measured at 4 and 12 weeks. The response of these patients was compared to the response of those given placebo in the first infusion.

TABLE 6

Response of Population Initially Failing to Respond to a Second Infusion of Anti-TNF-α Antibody cA2

|  | Percent Responding | | Percent in Remission | |
|---|---|---|---|---|
| Initial Treatment | 4 weeks | 12 weeks | 4 weeks | 12 weeks |
| Placebo | 60 | 56 | 47 | 33 |
| All cA2 | 34 | 28 | 17 | 7 |

As shown in Table 6, the subgroup of Crohn's disease patients that did not respond to the first infusion of cA2 was much less likely to respond to a second infusion than CD patients as a whole, for example, those administered a first placebo infusion. These results provide evidence for a clinical subtype of Crohn's Disease that is characterized as unlikely to respond to anti-Th1 cytokine therapy, such as an anti-TNF-α therapeutic. Analysis of γ-interferon levels demonstrated that those responding to the antibody therapy had higher levels of this cytokine, providing evidence for the involvement of distinct types of cytokine dysregulation in the inflammatory process in this Crohn's disease subtype.

EXAMPLE II

Diagnosing Clinical Subtypes of CD

This example demonstrates that the presence of pANCA or the presence of the TNF microsatellite haplotype a10b4c1d3e3 or a11b4c1d3e3 is diagnostic of an inferior clinical response to anti-Th1 cytokine therapy and that the presence of SAPPA is diagnostic of a superior clinical response to anti-Th1 cytokine therapy. This example further demonstrates that the presence of the homozygous TNF-β "1111 haplotype" is diagnostic of an inferior clinical response to anti-Th1 cytokine therapy.

Samples were analyzed for the presence or absence of pANCA and SAPPA and for the presence or absence of TNF microsatellite haplotypes a10b4c1d3e3 and a11b4c1d3e3 as described below using genomic DNA and serum obtained from peripheral blood prior to infusion with the anti-TNF-α antibody cA2 in 75 patients enrolled at centers in the USA. Prior to infusion, baseline CDAI, IDBQ and CRP levels were analyzed. At zero and four weeks after infusion with cA2, patients were re-evaluated, and the change in CDAI, IBDQ and CRP determined. A clinical response was defined as a drop in CDAI of at least 70. Remission, assessed at 4 weeks post-infusion, was defined as a CDAI of less than 150.

Stratification of CD patients according to pANCA status indicated that the pANCA-positive subgroup of CD has an inferior clinical response to anti-Th1 cytokine therapy. As shown in Table 7, the percentage of pANCA-positive CD patients clinically responsive to cA2 was about 35%, compared to a 60% clinical response for all CD treated with cA2. The percentage of pANCA-positive patients undergoing remission was only about 11% compared to 25% of treated CD patients not stratified by pANCA status. Similarly, the change in inflammatory activity, as indicated by ΔCRP, was significantly lower in the pANCA-positive subgroup (−0.3) than in all patients treated with cA2 (−1.1). Moreover, the magnitude and duration of response in pANCA-positive CD patients was diminished in comparison to other clinical subtypes, as shown by analysis of ΔCDAI and ΔIBDQ over a 12 week period (see FIG. 2). In sum, these results indicate that the presence of pANCA in a patient with CD can be used to diagnose a clinical subtype having an inferior clinical response to anti-Th1 cytokine therapy such as the anti-TNF-α antibody cA2.

The results shown in Table 7 also indicate that the presence of TNF microsatellite haplotype a10b4c1d3e3 or a11b4c1d3e3 was diagnostic of a subgroup of CD patients having an inferior clinical response to anti-Th1 cytokine therapy. The percentage of a10b4c1d3e3-positive CD patients clinically responsive to cA2 was only 25%, and the percentage of a11b4c1d3e3-positive CD patients was only 28%, compared to a 60% clinical response for all CD patients treated with cA2. Furthermore, only about 5% of a10b4c1d3e3-positive CD patients and about 14% of a11b4c1d3e3-positive CD patients went into remission after treatment with cA2, as compared to 25% of all treated CD patients not stratified by microsatellite haplotype. As a further indication of the inferior clinical response in these patients, the ΔCRP inflammatory index was significantly lower in the subgroup of a10b4c1d3e3 and a11b4c1d3e3-positive patients (−0.7 and 0, respectively) as compared to −1.1 for the entire group of CD patients treated with cA2. In sum, these

TABLE 7

Varying Clinical Responses of Crohn's Disease Patients to Anti-TNF-α Antibody cA2

| | % Resp | % Rem | CDAI* | ΔCDAI | ΔIBDQ | CRP* mg/dL | ΔCRP |
|---|---|---|---|---|---|---|---|
| Placebo | 17 | 0 | 290 | −16 | 11 | 1.0 | −0.3 |
| All cA2 treated | 60 | 25 | — | −97 | 32 | 1.8 | −1.1 |
| pANCA+ | 35 | 11 | 259 | −67 | 8 | 0.7 | −0.3 |
| pANCA− | — | 26 | 316 | −93 | 34.7 | 2.1 | −1.3 |
| +a10b4c1d3e3 | 25 | 5.3 | 298 | −70 | 29.8 | 1.6 | −0.7 |
| −a10b4c1d3e3 | — | 32.5 | 314 | −108 | 33.5 | 2.0 | −1.3 |
| +a11b4c1d3e3 | 28 | 14.3 | 340 | −36 | 6.3 | 0.6 | 0 |
| −a11b4c1d3e3 | — | 25.0 | 304 | −101 | 35.8 | 2.1 | −1.3 |
| SAPPA | 67 | 42 | — | −159 | 55 | 2.8 | −1.9 |

*determined prior to cA2 infusion results demonstrate that the presence of the a10b4c1d3e3 or a11b4c1d3e3 TNF microsatellite haplotype in a cohort of CD patients was diagnostic of clinical subgroups having an inferior response to anti-TNF-α therapy, as defined by changes in clinical disease and inflammation activity.

In contrast to the inferior clinical response to anti-Th1 cytokine therapy seen in the pANCA-positive subgroup, SAPPA-positive CD patients were characterized by a superior response to cA2, as compared with all CD patients treated with this therapeutic. As shown in Table 7, 42% of CD patients determined to have SAPPA went into remission compared with only 25% of all treated CD patients going into remission following infusion with cA2. These results were supported by a dramatic reduction in CDAI of −159 for SAPPA-positive CD patients in comparison with a drop of −97 for all patients treated irrespective of ANCA status. Similarly, the change in inflammatory index also was larger for SAPPA-positive patients (−1.9) as compared with all patients treated with cA2 (−1.1), indicating that the inflammation in the SAPPA-positive patients was responsive to cA2 treatment. Both the magnitude and duration of the response to cA2 were augmented in SAPPA-positive patients as compared to other clinical subtypes (see FIG. 2). In sum, these results indicate that the presence of SAPPA can be used to diagnose a clinical subtype of CD having a superior clinical response to anti-Th1 cytokine therapy.

Two other TNF haplotypes, including the CD-associated haplotype a2b1c2d4e1, were also analyzed. The TNFa2b1c2d4e1 haplotype, which occurred in about 25% of the patients studied, was diagnostic of a sustained response to cA2. In particular, while the percentage of a2b1c2d4e1-positive patients responding to cA2 was comparable to the response in the unstratified patient population at 4 weeks, the percentage of a2b1c2d4e1-positive patients responding was significantly greater than the response of the general population when assayed at 8 and 12 weeks. These results indicate that the presence of the TNFa2b1c2d4e1 haplotype is diagnostic of a clinical subtype of CD having a sustained superior response to anti-Th1 cytokine therapy.

The results summarized in Table 8 demonstrate that the presence of pANCA or the presence of the TNFa10b4c1d3e3 or TNFa11b4c1d3e3 haplotype is diagnostic of a clinical subtype of CD having an inferior clinical response to anti-Th1 cytokine therapy. These results further show that the presence of SAPPA is diagnostic of a clinical subtype of CD having a superior clinical response to anti-Th1 cytokine therapy.

TABLE 8

Clinical Subtypes of CD having Inferior and Superior Clinical Responses to Anti-TNF-α Therapy

| Clinical Response | Marker | Percent in Remission | ΔCDAI | ΔIBDQ | ΔCRP |
|---|---|---|---|---|---|
| Mixed | All cA2 treated | 25% | −97 | 32 | −1.1 |
| Inferior | pANCA | 11% | −67 | 8 | −0.3 |
| | +a10b4c1d3e3 | 5.3% | −70 | 29.8 | −0.7 |
| | +a11b4c1d3e3 | 14.3% | −36 | 6.3 | 0 |
| Superior | SAPPA | 42% | −159 | 55 | −1.9 |

The relationship between the antibody and genetic markers was analyzed in the cA2-treated population. Of twelve patients who were pANCA-positive, including several in the placebo group, eight had either the TNFa10b4c1d3e3 or a11b4c1d3e3 haplotype, suggesting that these haplotypes and pANCA-positivity may not be independent variables. Three of seven patients with the TNFa11b4c1d3e3 haplotype were pANCA-positive, and three of seven were SAPPA-positive. Of patients with the TNFa2b1c2d4e1 haplotype, two of sixteen were pANCA-positive, and seven of sixteen were SAPPA-positive. In view of these results, TNF microsatellite haplotype markers and the presence of pANCA or SAPPA can be used independently or in any combination to diagnose clinical subtypes of CD having particular clinical responses to anti-Th1 cytokine therapy.

Baseline serum C reactive protein (CRP) levels and IgG subclasses were analyzed in CD patients stratified according to the presence of the pANCA, SAPPA and TNF haplotype markers. Clinical subtypes of CD with an inferior clinical response had lower baseline CRP levels as compared to the general population of cA2-treated CD patients: the pANCA-positive subgroup had a CRP of 0.7; the a10b4c1d3e3-positive subgroup had a CRP of 1.6; and the a11b4c1d3e3 subgroup had a CRP of 0.6, compared to a CRP of 1.8 for all patients treated with cA2 (see Table 7). In contrast, the SAPPA-positive subgroup had an elevated baseline CRP level of 2.8.

IgG subclass ratios also were analyzed in pANCA-positive and SAPPA-positive CD patients. The IgG1:IgG2 ratio for the pANCA-positive clinical subtype of CD patients was determined to be greater than 1.5, while the ratio for the SAPPA-positive subtype was about 1. In sum, the results with baseline CRP levels and IgG1:IgG2 ratios provide evidence that the pANCA, SAPPA and TNF microsatellite haplotype CD clinical subtypes disclosed herein are characterized by different immune responses.

Figure 4A:
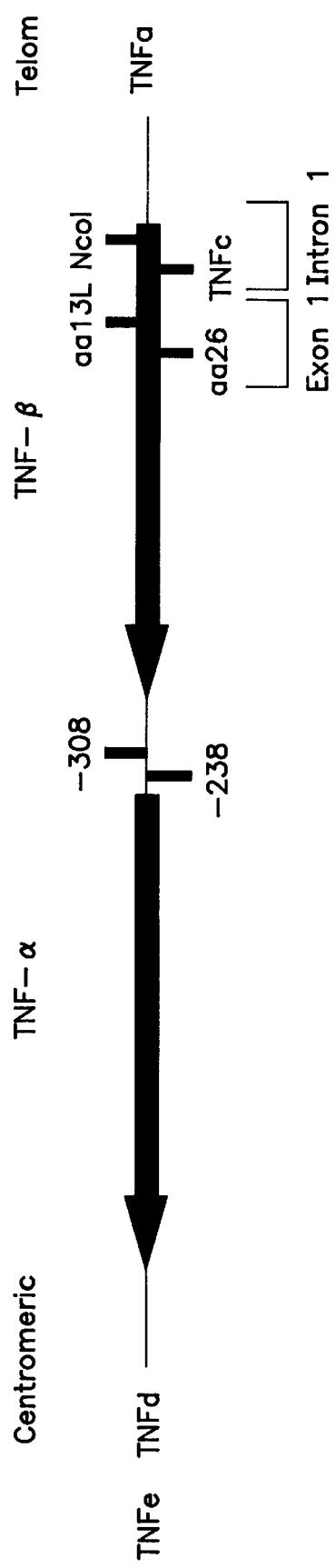
Figure 5A:
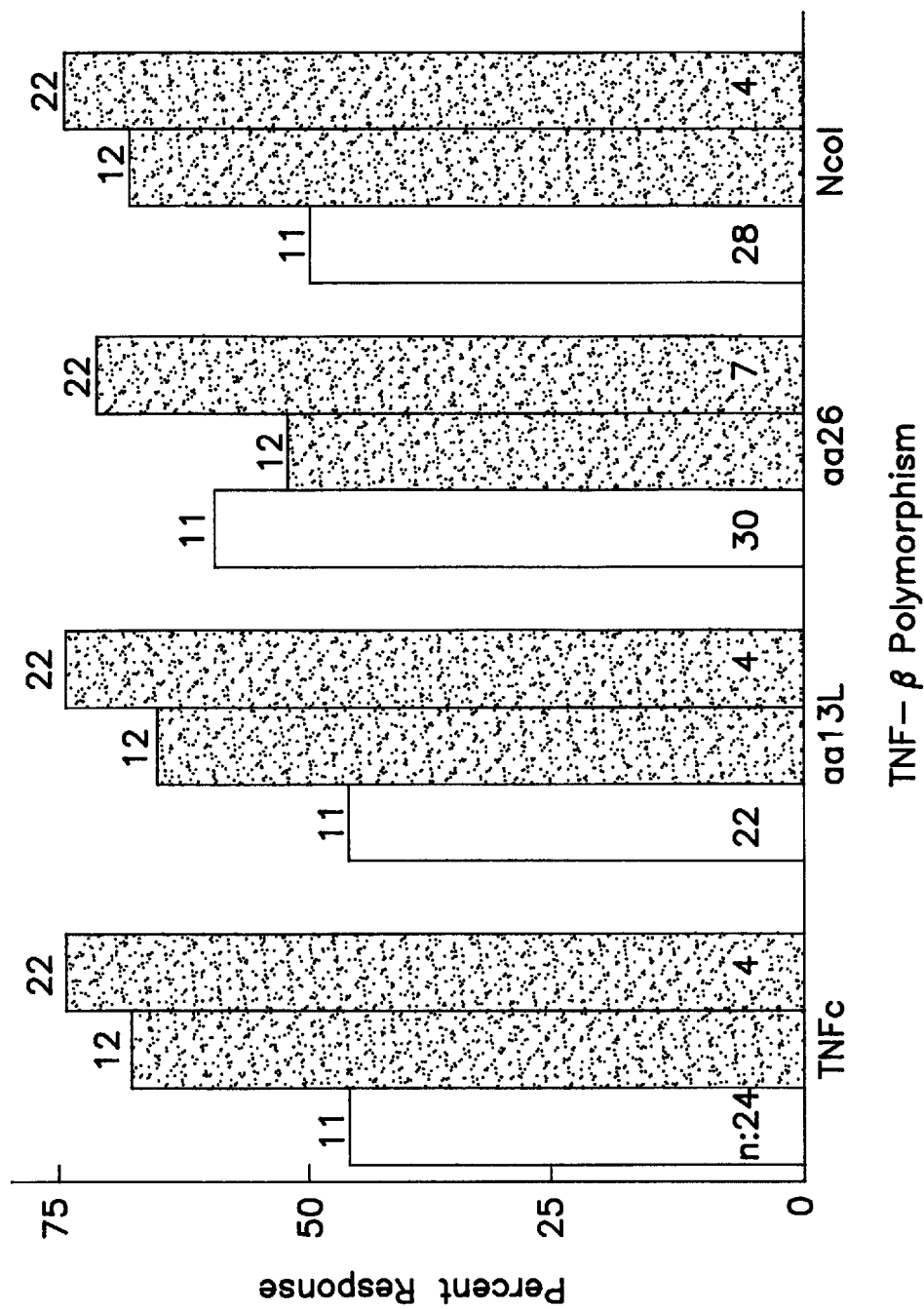
FIGS. 5A–C shows the response and ANCA status of CD patients subtyped according to genotype at four biallelic TNF-β polymorphic loci.

Additional biallelic loci within the TNF-α and TNF-β genes were analyzed for a correlation with response to cA2. As shown in FIG. 4A, four polymorphic loci are present in the TNF-β gene: TNFc in the first intron; the aa13 TNF-β leader sequence T/C polymorphism in exon 1; the aa26 C/A polymorphism in exon 1; and an NcoI restriction fragment length polymorphism (RFLP) in the first intron of TNF-β. The genotype of Crohn's disease patients treated with cA2 was analyzed at each of these four biallelic TNF-β loci. The results shown in FIG. 5A demonstrate that the percentage of patients with a clinical response to cA2 was greatest for patients having two copies of the rare allele at any one of the TNFc, aa13L, aa26 or NcoI TNF-β loci. The presence of a single copy of the rare allele at any one of these four TNF-β loci indicated a greater likelihood of clinical response than for that group of patients homozygous for the common allele. No correlation with a particular clinical response to the cA2 antibody was observed for the −238 and −308 polymorphisms within the TNF-α promoter or for several other polymorphisms studied, including the ICAM-1 $Arg^{241}$ and IL-10 microsatellite polymorphisms. These results indicate that the presence of a rare allele at any of the four TNF-β loci TNFc, aa13L, aa26 or NcoI is diagnostic of a superior clinical response to anti-Th1 cytokine therapy, with homozygosity for a rare allele predictive of an even better clinical response.

IgG1 to IgG2 ratios and baseline serum C reactive protein levels (CRP) were determined for each aa13L genotype. The IgG1:IgG2 ratio decreased with increasing number of copies of the rare aa13L allele, indicating that the homozygous rare aa13L genotype, which has the best response to cA2 therapy, is associated with the greatest Th1 cell involvement. Furthermore, CRP levels increased with increasing number of copies of the rare aa13L allele. In sum, these results provide evidence that the distinct genotypes at the aa13L TNF-β locus are characterized by different immune responses.

Figure 5B:
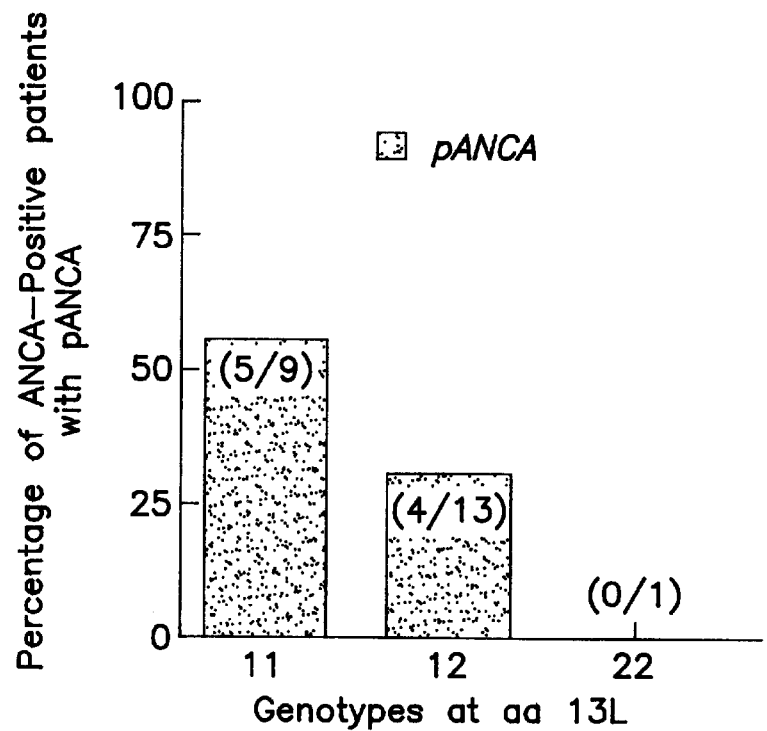
Figure 5C:
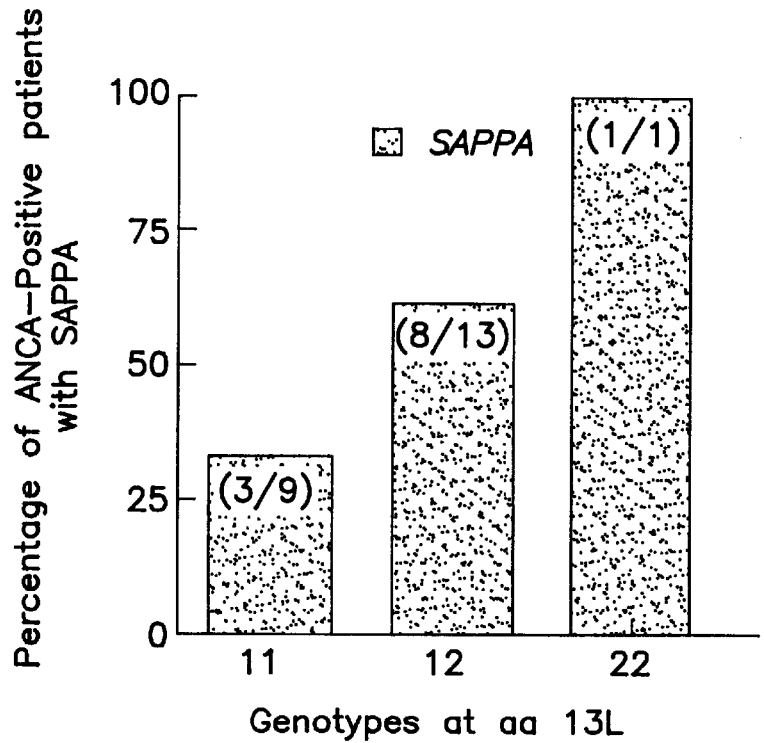

The relationship of the aa13L genotypes with pANCA and SAPPA serological markers was analyzed as shown in FIG. 5B. Patients having both common aa13L alleles ("11") were more frequently pANCA-positive than patients heterozygous at aa13L (left panel). These results suggest that the common "1" allele at the aa13L locus can be associated with pANCA. In view of these results, the presence of the common aa13 L allele and the presence of pANCA can be used independently or together to diagnose a clinical subtype of Crohn's disease having an inferior clinical response to anti-Th1 cytokine therapy.

Conversely, the rare aa13L allele can be associated with the presence of SAPPA. As shown in the right panel of FIG. 5B, the single patient with the "22" genotype was SAPPA-positive. Moreover, eight of thirteen patients with the "12" genotype were SAPPA-positive while a smaller proportion of those with the "11" genotype were SAPPA-positive (three of nine). Thus, the rare "2" allele at the aa13L locus can be associated with the presence of SAPPA, and these markers can be used independently or together to diagnose a clinical subtype of Crohn's disease having a superior clinical response to anti-Th1 cytokine therapy.

The combined genotypes at the TNFc, aa13L, aa26 and NcoI loci were analyzed in CD patients treated with cA2. The four locus TNF-β "1111" haplotype denotes that the more common of the two alleles is present at each of TNFc, aa13L, aa26 and NcoI loci; this homozygous haplotype was present in 9.2% of the 75 CD patients studied. As shown in FIG. 6A, none of the six CD patients with the homozygous 1111/1111 TNF-β haplotype had a clinical response to cA2 at four weeks. In contrast, approximately 60% of patients heterozygous ("1111/X") or lacking the 1111 haplotype ("X/X") responded to cA2 therapy at four weeks. These results indicate that a homozygous TNF-β 1111 haplotype is diagnostic of a clinical subtype of CD having an inferior clinical response to anti-Th1 cytokine therapy.

IgG1 to IgG2 ratios and baseline serum C reactive protein levels (CRP) were determined for each of the TNF-β four locus haplotypes. The six patients with the homozygous 1111/1111 haplotype had an IgG1:IgG2 ratio of about 2, as did the 25 patients with the heterozygous 1111/X haplotype. In patients lacking the 1111 haplotype, the IgG1:IgG2 ratio was reduced to about 1.5. Thus, a relatively high IgG1:IgG2 ratio characteristic of Th2 cell involvement is associated with the poorly responding 1111/1111 clinical subtype of CD. Distinct CRP levels also were seen in patients subtyped according to the TNF-β four locus haplotype, with lower CRP levels associated with the presence of the 1111 haplotype. These results provide evidence for different immune responses in patients stratified according to the presence or absence of the TNF-β four locus haplotype.

Figure 6B:
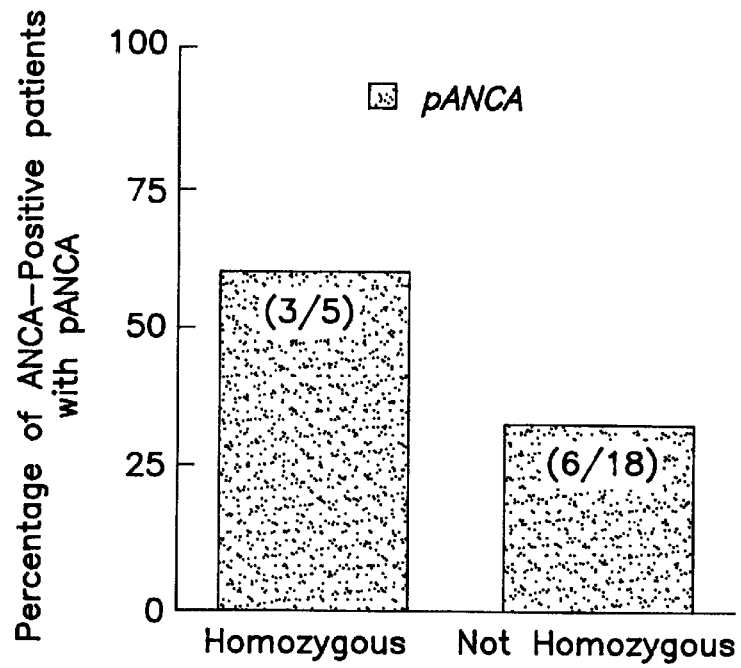
Figure 6C:
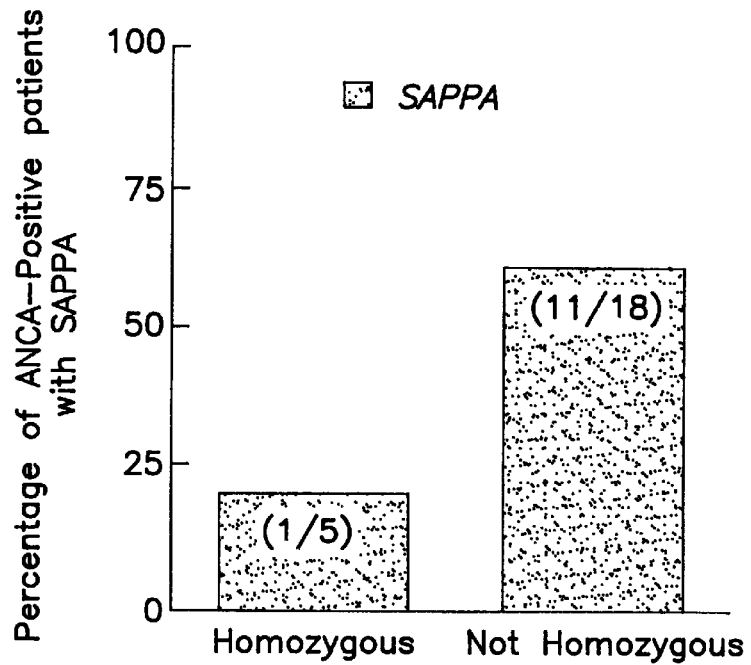

The relationship of the TNF-β haplotype with pANCA and SAPPA serological markers was also analyzed. As shown in the left panel of FIG. 6B, three of five patients homozygous for the TNF-β 1111 haplotype were pANCA-positive. A smaller proportion of those having zero or one copy of the TNF-β 1111 haplotype (six of 18) were pANCA-positive. These results demonstrate that the TNF-β 1111 haplotype and pANCA may not be independent markers of an inferior clinical response to anti-Th1 cytokine therapy and indicate that the TNF-β 1111 haplotype and the presence of pANCA can be used independently or together to predict an inferior clinical response to anti-Th1 cytokine therapy.

EXAMPLE III

Determination of Patient ANCA Status

This example demonstrates the determination of patient ANCA status by ELISA and indirect immunofluorescence.

Fixed Neutrophil ELISA for Determining ANCA Levels

A fixed neutrophil enzyme-linked immunosorbent assay was used to detect ANCA as described in Saxon et al., supra, 1990, which is incorporated herein by reference, and all samples were analyzed in a blinded fashion. Briefly, microliter plates were coated with $2.5 \times 10^5$ neutrophils per well and treated with 100% methanol to fix the cells. Cells were incubated with 0.25% bovine serum albumin (BSA) in phosphate-buffered saline to block nonspecific antibody binding. Next, control and coded sera were added at a 1:100 dilution to the bovine serum/phosphate-buffered saline blocking buffer. Alkaline phosphatase-conjugated goat $F(ab')_2$ anti-human immunoglobulin G antibody (γ-chain specific; Jackson Immunoresearch Labs, Inc., West Grove, Pa.) was added at a 1:1000 dilution to label neutrophil-bound antibody. A solution of p-nitrophenol phosphate substrate was added, and color development was allowed to proceed until absorbance at 405 nm in the positive control wells was 0.8–1.0 optical density units greater than the absorbance in blank wells.

Sera from 20 normal individuals was used to define negative binding. The mean reading of the normal control sera was about 5 to 15 ELISA units; the mean plus two standard deviations ranged from 10 to 25 ELISA units. Standard binding of pooled, well-characterized pANCA-positive UC patient sera was set to 100 ELISA units, and results with test patient sera were expressed relative to this standard positive binding. Samples were defined to be ANCA-positive when ELISA levels were greater than two standard deviations (SD) above the mean of the pooled normal control sera. Low level ANCA-positivity was defined as less than about 40 ELISA units.

Indirect Immunofluorescence Assay for Determination of ANCA Staining Pattern

Indirect immunofluorescent staining was performed on samples that were ANCA-positive by ELISA to determine whether the predominant staining pattern was perinuclear (pANCA); cytoplasmic (cANCA); or diffuse (SAPPA). Glass slides containing approximately 100,000 neutrophils per slide were prepared by cytocentrifugation (Shandon Cytospin, Cheshire, England). The slides were subsequently fixed in 100% methanol, air-dried and stored at −20° C. The fixed neutrophils were incubated with human sera diluted 1:20 in PBS with 0.25% bovine serum albumin and 0.2% sodium azide. The reaction was visualized with a 1:1000 dilution of fluorescein-labeled F(ab')$_2$ γ chain-specific antibody as described in Saxon et al., supra, 1990. Slides were examined using an epifluorescence-equipped Olympus BH-2 microscope (Olympus, Lake Success, N.Y.).

Figure 1A:
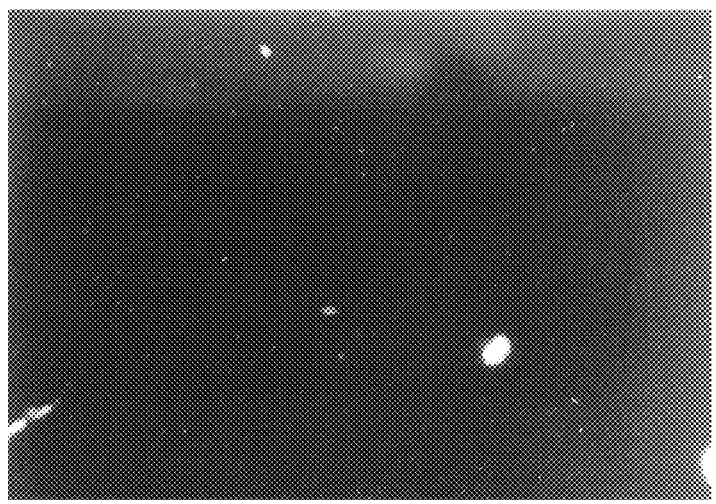
FIGS. 1A–C shows immunofluorescence of methanol-fixed neutrophil with human sera. Panel (a) shows an ANCA-negative staining pattern; panel (b) shows the pANCA staining pattern; and panel (c) shows the SAPPA staining pattern.
Figure 1B:
Figure 1C:
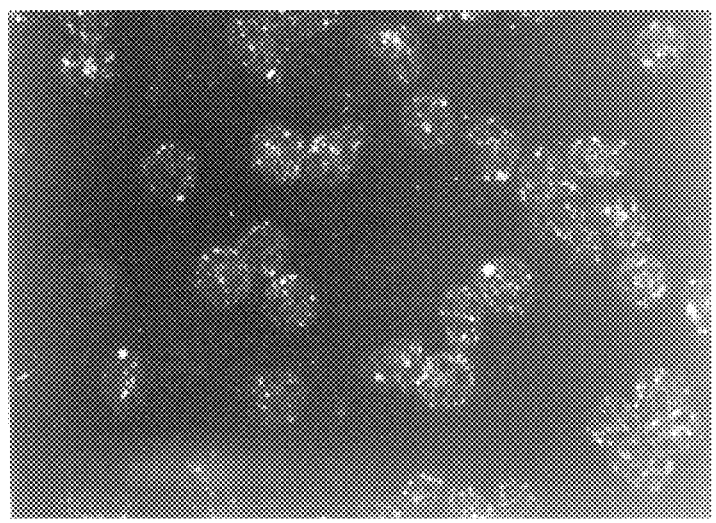

Upon indirect immunofluorescence, ANCA-positive samples gave several distinct staining patterns as shown in FIG. 1. In contrast to the absence of staining seen with sera that was ANCA-negative, i.e. less than two standard deviations above the mean of normal sera as shown in panel (a), ANCA-positive samples produced distinct patterns of reactivity with human neutrophil. Nuclear/perinuclear staining of ANCA-positive samples is shown in panel (b) and is designated pANCA. A distinct, diffuse staining pattern with speckling over the entire neutrophil was produced by some low-level ELISA-positive samples (SAPPA). Panel (c) shows representative staining for this SAPPA pattern. A distinct cytoplasmic staining pattern was evident with other ANCA-positive sera (cANCA; data not shown).

EXAMPLE IV

PCR Analysis of TNF Microsatellite Alleles

This example demonstrates that PCR analysis can be used to distinguish alleles at the TNFa, TNFb, TNFc, TNFd and TNFe loci based on size.

Oligonucleotides used as PCR primers for TNF microsatellite analysis, shown in Table 9, were synthesized at the Cedars-Sinai Medical Center core DNA synthesis facility from sequences published in Udalova et al., supra, 1993. Genomic DNA from patients and controls was amplified using a two-step PCR procedure as follows. The first PCR was performed with primers SEQ ID NO:1 and SEQ ID NO:2 (for TNFa and TNFb), SEQ ID NO:7 and SEQ ID NO:10 (for TNFd and TNFe), and SEQ ID NO:5 and SEQ ID NO:6 (for TNFc). Primer pairs at a final concentration of 0.15 μmol/L each were added in a total reaction volume of 20 μL with 10 mmol/L Tris-HCl (pH 8.3); 50 mmol/L KCl; 2 mmol/L MgCl$_2$; 200 μmol/L each deoxyadenosine triphosphate, deoxyguanosine triphosphate, deoxycytidine triphosphate, and deoxyribosylthymine triphosphate; 100–500 ng genomic DNA; and 1 U Amplitaq DNA polymerase (Perkin-Elmer Cetus, Norwalk, Conn.) PCR was performed in a 480 thermal cycler (Perkin-Elmer Cetus) under the following conditions: 94° C. for 7 minutes and then 25 cycles at 94° C. for 60 seconds, 60° C. for 60 seconds, and 72° for 60 seconds followed by a 5-minute extension at 72° C.

During the second PCR, DNA fragments at each TNF microsatellite loci were amplified separately. Two microliters of the first PCR reaction was added to reagents in the same final concentrations as in the first PCR to a total volume of 20 μl. For TNFa and TNFb typing, concentrations were the same as in the first PCR in a total volume of 20 μl. For TNFa, primer SEQ ID NO: 3 was added, and for TNFb typing, primer SEQ ID NO:4 was added. For TNFd typing, primer SEQ ID NO:8 was added to the SEQ ID NO:7 and SEQ ID NO:10 reaction. For TNFe typing, primer SEQ ID NO:9 was added to the SEQ ID NO:7 and SEQ ID NO:10 reaction. For TNFc, primers SEQ ID NO:5 and SEQ ID NO:6 were readded to a final concentration of 0.15 μmol/L. Deoxyguanosine triphosphate, deoxycytidine triphosphate, and deoxyribosylthymine triphosphate were added to the same final concentration as in the first PCR reaction. Deoxyadenosine triphosphate were replaced with 5 μCi 35S-α-deoxyadenosine triphosphate in the second PCR. After 7 minutes at 94° C., 6 cycles of PCR were completed at the same times and temperatures as the first PCR, followed by a 5-minute extension at 72° C.

After the second round of amplification, 3 μl of each sample was denatured by boiling and electrophoresed on a 7 mol/l urea, 6% polyacrylamide, 0.4-mm sequencing gel at 1500 V. Gels were run with a 35S-α-deoxyadenosine triphosphate-labeled pGEM-3Zs (+) control DNA sequencing marker (Promega, Madison, Wis.) to size fragments. Two-step PCR was also performed with genomic DNA from CEPH/ASHI cell lines (provided by Pat Concannon and Dolly Tyan) previously typed at all 5 TNF microsatellite loci as controls.

TABLE 9

Oligonucleotide Primer Sequences for Amplification of TNF Microsatellite loci

| TNF loci | SEQ ID NO: Primer sequence | |
|---|---|---|
| a and b | SEQ ID NO: 1 | 5'-GCACTCCAGCCTAGGCCACAGA-3' |
|  | SEQ ID NO: 2 | 5'-GCCTCTAGATTTCATCCAGCCACA-3' |
| a only | SEQ ID NO: 2 | 5'-GCCTCTAGATTTCATCCAGCCACA-3' |
|  | SEQ ID NO: 3 | 5'-CCTCTCTCCCCTGCAACACACA-3' |
| b only | SEQ ID NO: 1 | 5'-GCACTCCAGCCTAGGCCACAGA-3' |
|  | SEQ ID NO: 4 | 5'-GTGTGTGTTGCAGGGGAGAGAG-3' |
| c only | SEQ ID NO: 5 | 5'-GGTTTCTCTGACTGCATCTTGTCC-3' |
|  | SEQ ID NO: 6 | 5'-TCATGGGGAGAACCTGCAGAGAA-3' |
| d and e | SEQ ID NO: 7 | 5'-AGATCCTTCCCTGTGAGTTCTGCT-3' |
|  | SEQ ID NO: 10 | 5'-TGAGACAGAGGATAGGAGAGACAG-3' |
| d only | SEQ ID NO: 7 | 5'-AGATCCTTCCCTGTGAGTTCTGCT-3' |
|  | SEQ ID NO: 8 | 5'-CATAGTGGGACTCTGTCTCCAAAG-3' |
| e only | SEQ ID NO: 9 | 5'-GTGCCTGGTTCTGGAGCCTCTC-3' |
|  | SEQ ID NO: 10 | 5'-TGAGACAGAGGATAGGAGAGACAG-3' |

Internal standards were necessary for unambiguous allele interpretations, particularly at the TNFb and TNFd loci. PCR product from at least one standard cell line per TNF microsatellite locus was electrophoresed with the sample DNA. Gels were subsequently dried and autoradiographed with XAR-5 X-ray film (Kodak Corp., Rochester, N.Y.) and one intensifying screen at −70° C. for 48 to 72 hours. Microsatellite alleles differ by one dinucleotide repeat for TNFa, TNFe, TNFd, and TNFe. For TNFb, alleles differ by 1 or 2 bases as reported in Udalova et al., supra, 1993). For each of the TNF microsatellite alleles, the smallest allele is termed 1 with larger alleles numbered consecutively.

EXAMPLE V

Analysis of TNF-β Four Locus Haplotype

This example demonstrates that the common and rare alleles can be distinguished at the TNFc, aa13L, aa26 and NcoI loci.

Analysis of the TNFc Polymorphism

TNFc alleles were analyzed as described above in Example IV.

Analysis of the aa13 L and aa26 Polymorphisms

For determination of alleles at the aa13L and aa26 loci, allele-specific oligonucleotide hybridization was performed using an initial non-stringent hybridization with radiolabeled probe followed by washing with 3.0 M tetramethylammonium chloride (TMAC) to control the stringency of the hybridization as described in Wood et al., *Proc. Natl. Acad. Sci.*, USA 82: 1585–1588 (1985), which is incorporated herein by reference.

Briefly, Hybond-N+ filters (Amersham) were wet with distilled water, and DNA was applied to the filters using a vacuum manifold. After applying PCR product with 200 μl 10×SSC to the filter under vacuum, the filter was denatured with 0.5 N NaOH/1.5 M NaCl for 10 minutes and neutralized with 0.5 M Tris-HCl/1.5 M NaCl for 5 minutes. Filters were dried under a heat lamp for 30 minutes prior to baking in vacuo at 80° C. for two hours.

The filters were prehybridized in 6×SSPE/0.5% SDS/5× Denhardt's solution/100 μg/ml denatured salmon sperm DNA for at least 1 hour at 37° C. The appropriate 19-mer allele-specific oligonucleotide was radiolabeled and incubated with the filter at 37° C. overnight. For analysis of the aa13L leader sequence polymorphisms, the allele-specific oligonucleotide CCAAGGGTGTGTGGCACCA (SEQ ID NO: 15) was used for specific detection of the common or "1" aa13L allele, which has a "T" at position 207 of the TNF-β cDNA nucleotide sequence shown in FIG. 4B. The allele-specific oligonucleotide CCAAGGGTGCGTGGC ACCA (SEQ ID NO: 16) was used for specific detection of the rare or "2" aa13L allele, which has a "C" at position 207 of the TNF-β cDNA nucleotide sequence shown in FIG. 4B.

Analysis of the aa26 locus was performed with oligonucleotides SEQ ID NOS: 17 and 18. The allele-specific oligonucleotide CCCACAGCACCCTCAAACC (SEQ ID NO: 17) was used for specific detection of the common or "1" aa26 allele, which has a "C" at position 349 of the TNF-β nucleotide sequence shown in FIG. 4B. The allele-specific oligonucleotide CCCACAGCAACCTCAAACC (SEQ ID NO: 18) was used for specific detection of the rare or "2" allele, which has an "A" at position 349 of the TNF-β nucleotide sequence shown in FIG. 4B.

Following hybridization with the allele-specific oligonucleotide probe, filters were washed twice with 6×SSPE/ 0.5% SDS for 10 minutes. Subsequently, filters were washed twice at high stringency with 3.0 M TMAC/2 mM EDTA/50 mM Tris-HCl (pH 8.0) at 58.5° C. for 30 minutes each. After drying, the filers were subject to autoradiography at −70° C.

Analysis of the NcoI Restriction Fragment Length Polymorphism

The presence or absence of the NcoI restriction fragment length polymorphism was analyzed by preparing a PCR product containing the polymorphic region followed by restriction endonuclease digestion with NcoI. Briefly, primers CCCGTGCTTCGTGCTTTGG (SEQ ID NO: 19) and GAG TTCTGCTTGCTGGGGTCTCCT (SEQ ID NO: 20) were used to amplify genomic DNA as described above. Subsequently, 5 μl of the PCR product was digested with 5 units NcoI at 37° C. for 2 hours. The restriction digestion products were analyzed by electrophoresis on a 1.2% agarose gel. The common or "1" allele was indicated by a NcoI restriction digestion product of 970 bp fragment. The rare or "2" allele was indicated by NcoI restriction digestion products of about 770 bp and 200 bp.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of diagnosing a clinical subtype of Crohn's disease (CD) having an inferior clinical response to anti-Th1 cytokine therapy, comprising determining whether perinuclear anti-neutrophil antibody (pANCA) is present in a patient with CD,
    wherein the presence of pANCA indicates a clinical subtype of CD having an inferior clinical response to anti-Th1 cytokine therapy.

2. The method of claim 1, further comprising determining the presence or absence of a TNFa10b4c1d3e3 haplotype in said patient with CD,
    wherein the presence of pANCA indicates a clinical subtype of CD having an inferior clinical response to anti-Th1 cytokine therapy and
    the presence of said TNFa10b4c1d3e3 haplotype independently indicates a clinical subtype of CD having an inferior clinical response to anti-Th1 cytokine therapy.

3. The method of claim 1, further comprising determining the presence or absence of a TNFa11b4c1d3e3 haplotype in said patient with CD,
    wherein the presence of pANCA indicates a clinical subtype of CD having an inferior clinical response to anti-Th1 cytokine therapy and
    the presence of said TNFa11b4c1d3e3 haplotype independently indicates a clinical subtype of CD having an inferior clinical response to anti-Th1 cytokine therapy.

4. The method of claim 1, further comprising determining the presence or absence of a TNFa10b4c1d3e3 haplotype in said patient with CD and determining the presence or absence of a TNFa11b4c1d3e3 haplotype in said patient with CD,
    wherein the presence of pANCA indicates a clinical subtype of CD having an inferior clinical response to anti-Th1 cytokine therapy, the presence of said TNFa10b4c1d3e3 haplotype independently indicates a clinical subtype of CD having an inferior clinical response to anti-Th1 cytokine therapy and the presence of said TNFa11b4c1d3e3 haplotype independently indicates a clinical subtype of CD having an inferior clinical response to anti-Th1 cytokine therapy.

5. The method of claim 1, wherein determining the presence of pANCA comprises the steps of:

(a) obtaining a serum sample from said patient with CD;

(b) determining by non-histological means whether anti-neutrophil cytoplasmic antibody (ANCA) is detectable in patient sera diluted at least about 100-fold; and (c) assaying for the presence or absence of a pANCA staining pattern, wherein detection of ANCA in patient sera diluted at least about 100-fold and the presence of a pANCA staining pattern indicate the presence of pANCA, provided that said detection of ANCA is not by histological means.

6. The method of claim 2, wherein determining the presence of pANCA comprises the steps of:

(a) obtaining a serum sample from said patient with CD;

(b) contacting the serum sample diluted at least about 100-fold with antigen specific for ANCA under conditions suitable to form a first complex of antigen and ANCA;

(c) detecting the presence or absence of said first complex;

(d) contacting an appropriate dilution of the serum sample with antigen specific for ANCA under conditions suitable to form a second complex of antigen and ANCA; and (e) assaying for the presence or absence of a pANCA staining pattern by detecting the presence or absence of said second complex, wherein the presence of said first complex and the presence of a pANCA staining pattern indicate the presence of pANCA, provided that detection of said first complex is not by histological means.

7. The method of claim 6, wherein said antigen specific for ANCA is neutrophil.

8. The method of claim 6, wherein the serum sample in step (b) is diluted 100-fold.

9. The method of claim 6, wherein the presence or absence of said first complex is detected in an immunoassay.

10. The method of claim 9, wherein said immunoassay is an enzyme-linked immunosorbent assay.

11. A method of diagnosing a clinical subtype of Crohn's disease having a superior clinical response to anti-Th1 cytokine therapy, comprising determining whether SAPPA is present in a patient with CD, wherein the presence of SAPPA indicates a clinical subtype of CD having a superior clinical response to anti-Th1 cytokine therapy.

12. The method of claim 11, wherein determining the presence of SAPPA comprises the steps of:

(a) obtaining a serum sample from said patient with CD;

(b) determining by non-histological means the level of ANCA-positivity in patient sera diluted at least about 100-fold; and (c) assaying for the presence or absence of a SAPPA staining pattern, wherein low level ANCA-positivity in patient sera diluted at least about 100-fold and the presence of a SAPPA staining pattern indicate the presence of SAPPA, provided that said detection of ANCA is not by histological means.

13. The method of claim 11, wherein determining the presence of SAPPA comprises the steps of:

(a) obtaining a serum sample from said patient with CD;

(b) contacting the serum sample diluted at least about 100-fold with antigen specific for ANCA under conditions suitable to form a first-complex of antigen and ANCA;

(c) detecting the presence or absence of said first complex;

(d) contacting an appropriate dilution of the serum sample with antigen specific for ANCA under conditions suitable to form a second complex of antigen and ANCA; and (e) assaying for the presence or absence of a SAPPA staining pattern by detecting the presence or absence of said second complex, wherein low level ANCA-positivity indicated by a low level of said first complex and the presence of a SAPPA staining pattern indicate the presence of SAPPA, provided that detection of said first complex is not by histological means.

14. The method of claim 13, wherein said antigen specific for ANCA is neutrophil.

15. The method of claim 13, wherein the serum sample in step (b) is diluted 100-fold.

16. The method of claim 13, wherein the presence or absence of said first complex is detected in an immunoassay.

17. The method of claim 16, wherein said immunoassay is an enzyme-linked immunosorbent assay.

18. A method of diagnosing a clinical subtype of Crohn's disease having a superior or inferior clinical response to anti-Th1 cytokine therapy, comprising (a) determining whether SAPPA is present in a patient with CD and (b) determining the presence or absence of a TNFa10b4c1d3e3 haplotype in said patient with CD, wherein the presence of SAPPA in the absence of said TNFa10b4c1d3e3 haplotype indicates a clinical subtype of CD having a superior clinical response to anti-Th1 cytokine therapy and the presence of said TNFa10b4c1d3e3 haplotype in the absence of said SAPPA indicates a clinical subtype of CD having an inferior clinical response to anti-Th1 cytokine therapy.

19. A method of diagnosing a clinical subtype of Crohn's disease having a superior or inferior clinical response to anti-Th1 cytokine therapy, comprising (a) determining whether SAPPA is present in a patient with CD and (b) determining the presence or absence of a TNFa11b4c1d3e3 haplotype in said patient with CD, wherein the presence of SAPPA in the absence of said TNFa11b4c1d3e3 haplotype indicates a clinical subtype of CD having a superior clinical response to anti-Th1 cytokine therapy and the presence of said TNFa11b4c1d3e3 haplotype in the absence of said SAPPA indicates a clinical subtype of CD having an inferior clinical response to anti-Th1 cytokine therapy.

20. A method of diagnosing a clinical subtype of Crohn's disease having a superior or inferior clinical response to anti-Th1 cytokine therapy, comprising (a) determining whether SAPPA is present in a patient with CD;
(b) determining the presence or absence of a TNFa10b4c1d3e3 haplotype in said patient with CD; and
(c) determining the presence or absence of a TNFa11b4c1d3e3 haplotype in said patient with CD,
wherein the presence of SAPPA in the absence of said TNFa10b4c1d3e3 and TNFa11b4c1d3e3 haplotypes indicates a clinical subtype of CD having a superior clinical response to anti-Th1 cytokine therapy,
the presence of said TNFa10b4c1d3e3 haplotype in the absence of said SAPPA indicates a clinical subtype of CD having an inferior clinical response to anti-Th1 cytokine therapy and
the presence of said TNFa11b4c1d3e3 haplotype in the absence of said SAPPA independently indicates a clinical subtype of CD having an inferior clinical response to anti-Th1 cytokine therapy.

21. A method of diagnosing a clinical subtype of CD having an inferior clinical response to anti-Th1 cytokine therapy, comprising determining the presence or absence of at least two TNF microsatellite alleles selected from the group consisting of TNFa10, TNFb4, TNFc1, TNFd3 and TNFe3 in a patient with an established diagnosis of CD,
wherein the presence of an allelic combination comprising at least two of said alleles is diagnostic of a clinical subtype of CD having an inferior clinical response to anti-Th1 cytokine therapy.

22. The method of claim 21, comprising detecting at least three TNF microsatellite alleles selected from the group consisting of TNFa10, TNFb4, TNFc1, TNFd3 and TNFe3 in said patient with an established diagnosis of CD,
wherein the presence of an allelic combination comprising at least three of said alleles is diagnostic of a clinical subtype of CD having an inferior clinical response to anti-Th1 cytokine therapy.

23. A method of diagnosing a clinical subtype of CD having an inferior clinical response to anti-Th1 cytokine therapy, comprising determining the presence or absence of a TNFa10b4c1d3e3 haplotype in a patient with an established diagnosis of CD,
wherein the presence of said TNFa10b4c1d3e3 haplotype is diagnostic of a clinical subtype of CD having an inferior clinical response to anti-Th1 cytokine therapy.

24. The method of claim 23, wherein determining the presence absence of a TNFa10b4c1d3e3 haplotype comprises:
(a) obtaining material comprising nucleic acid including TNFa, TNFb, TNFc, TNFd and TNFe loci from said patient;
(b) enzymatically amplifying said nucleic acid using pairs of oligonucleotide primers complementary to nucleotide sequences flanking each of said TNFa, TNFb, TNFc, TNFd and TNFe loci to produce amplified products including TNFa, TNFb, TNFc, TNFd or TNFe; and
(c) electrophoresing said amplified products to identify said TNFa10b4c1d3e3 haplotype.

25. The method of claim 24, wherein one or more of said oligonucleotide primers are selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

26. The method of claim 25, wherein a first pair of oligonucleotide primers SEQ ID NO: 2 and SEQ ID NO: 3 produce amplified product including locus TNFa,
a second pair of oligonucleotide primers SEQ ID NO: 1 and SEQ ID NO: 4 produce amplified product including locus TNFb,
a third pair of oligonucleotide primers SEQ ID NO: 5 and SEQ ID NO: 6 produce amplified product including locus TNFc,
a fourth pair of oligonucleotide primers SEQ ID NO: 7 and SEQ ID NO: 8 produce amplified product including locus TNFd and
a fifth pair of oligonucleotide primers SEQ ID NO: 9 and SEQ ID NO: 10 produce amplified product including locus TNFe.

27. The method of claim 23, wherein determining the presence or absence of a TNFa10b4c1d3e3 haplotype comprises:
(a) obtaining material comprising nucleic acid including TNFa, TNFb, TNFc, TNFd and TNFe loci from said patient;
(b) enzymatically amplifying said nucleic acid using pairs of oligonucleotide primers complementary to nucleotide sequences flanking each of said TNFa, TNFb, TNFc, TNFd and TNFe loci to produce amplified products including TNFa, TNFb, TNFc, TNFd or TNFe; and
(c) sequencing said amplified products to identify said TNFa10b4c1d3e3 haplotype.

28. The method of claim 23, further comprising determining the presence or absence of a TNFa11b4c1d3e3 haplotype in said patient with an established diagnosis of CD,
wherein the presence of said TNFa10b4c1d3e3 haplotype is diagnostic of a clinical subtype of CD having an inferior clinical response to anti-Th1 cytokine therapy and
the presence of said TNFa11b4c1d3e3 haplotype independently is diagnostic of a clinical subtype of CD having an inferior clinical response to anti-Th1 cytokine therapy.

29. A method of diagnosing a clinical subtype of CD having an inferior clinical response to anti-Th1 cytokine therapy, comprising determining the presence or absence of at least two TNF microsatellite alleles selected from the group consisting of TNFa11, TNFb4, TNFc1, TNFd3 and TNFe3 in a patient with an established diagnosis of CD,
wherein the presence of an allelic combination comprising at least two of said alleles is diagnostic of a clinical subtype of CD having an inferior clinical response to anti-Th1 cytokine therapy.

30. The method of claim 29, comprising detecting at least three TNF microsatellite alleles selected from the group consisting of TNFa11, TNFb4, TNFc1, TNFd3 and TNFe3 in said patient with an established diagnosis of CD,
wherein the presence of an allelic combination comprising at least three of said alleles is diagnostic of a clinical subtype of CD having an inferior clinical response to anti-Th1 cytokine therapy.

31. A method of diagnosing a clinical subtype of CD having an inferior clinical response to anti-Th1 cytokine therapy, comprising determining the presence or absence of a TNFa11b4c1d3e3 haplotype in a patient with an established diagnosis of CD,
wherein the presence of said TNFa11b4c1d3e3 haplotype is diagnostic of a clinical subtype of CD having an inferior clinical response to anti-Th1 cytokine therapy.

32. The method of claim 31, wherein determining the presence or absence of a TNFa11b4c1d3e3 haplotype comprises:

(a) obtaining material comprising nucleic acid including TNFa, TNFb, TNFc, TNFd and TNFe loci from said patient;

(b) enzymatically amplifying said nucleic acid using pairs of oligonucleotide primers complementary to nucleotide sequences flanking each of said TNFa, TNFb, TNFc, TNFd and TNFe loci to produce amplified products including TNFa, TNFb, TNFc, TNFd or TNFe; and (c) electrophoresing said amplified products to identify said TNFa11b4c1d3e3 haplotype.

33. The method of claim 32, wherein one or more of said oligonucleotide primers are selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

34. The method of claim 33, wherein a first pair of oligonucleotide primers SEQ ID NO: 2 and SEQ ID NO: 3 produce amplified product including locus TNFa, a second pair of oligonucleotide primers SEQ ID NO: 1 and SEQ ID NO: 4 produce amplified product including locus TNFb, a third pair of oligonucleotide primers SEQ ID NO: 5 and SEQ ID NO: 6 produce amplified product including locus TNFc, a fourth pair of oligonucleotide primers SEQ ID NO: 7 and SEQ ID NO: 8 produce amplified product including locus TNFd and a fifth pair of oligonucleotide primers SEQ ID NO: 9 and SEQ ID NO: 10 produce amplified product including locus TNFe.

35. The method of claim 31, wherein determining the presence or absence of a TNFa11b4c1 d3e3 haplotype comprises:

(a) obtaining material comprising nucleic acid including TNFa, TNFb, TNFc, TNFd and TNFe loci from said patient;

(b) enzymatically amplifying said nucleic acid using pairs of oligonucleotide primers complementary to nucleotide sequences flanking each of said TNFa, TNFb, TNFc, TNFd and TNFe loci to produce amplified products including TNFa, TNFb, TNFc, TNFd or TNFe; and (c) sequencing said amplified products to identify said TNFa11b4c1d3e3 haplotype.

36. A method of diagnosing a clinical subtype of CD having an inferior clinical response to anti-Th1 cytokine therapy, comprising determining the presence or absence of a homozygous TNF-β 1111 haplotype at the TNFc, aa13L, aa26 and NcoI loci in a patient with CD, wherein the presence of said homozygous TNF-β 1111 haplotype is diagnostic of a clinical subtype of CD having an inferior clinical response to anti-Th1 cytokine therapy.

37. A method of diagnosing a clinical subtype of CD having a superior or inferior clinical response to anti-Th1 cytokine therapy, comprising the steps of:

(a) determining whether SAPPA is present in a patient with CD;

(b) determining whether pANCA is present in said patient with CD;

(c) determining the presence or absence of a TNFa10b4c1d3e3 haplotype in said patient with CD;

(d) determining the presence or absence of a TNFa11b4c1d3e3 haplotype in said patient with CD; and (e) determining the presence or absence of the homozygous TNF-β 1111 haplotype at the TNFc, aa13L, aa26 and NcoI loci in said patient with CD, wherein the presence of SAPPA in the absence of said TNFa10b4c1d3e3, TNFa10b4c1d3e3 and TNF-β 1111 haplotypes is diagnostic of a clinical subtype of CD having a superior clinical response to anti-Th1 cytokine therapy, the presence of pANCA in the absence of said SAPPA is diagnostic of a clinical subtype of CD having an inferior clinical response to anti-Th1 cytokine therapy, the presence of said TNFa10b4c1d3e3 haplotype in the absence of said SAPPA independently is diagnostic of a clinical subtype of CD having an inferior clinical response to anti-Th1 cytokine therapy, the presence of said TNFa11b4c1d3e3 haplotype in the absence of said SAPPA independently is diagnostic of a clinical subtype of CD having an inferior clinical response to anti-Th1 cytokine therapy and the presence of said homozygous TNF-β 1111 haplotype in the absence of said SAPPA independently is diagnostic of a clinical subtype of CD having an inferior clinical response to anti-Th1 cytokine therapy.

* * * * *

UNITED STATES PATENT AND TRADEMARK OFFICE
CERTIFICATE OF CORRECTION

PATENT NO. : 6,183,951 B1
DATED : February 6, 2001
INVENTOR(S) : Plevy et al.

It is certified that error appears in the above-identified patent and that said Letters Patent is hereby corrected as shown below:

Column 53,
Line 47, please delete "absence", replace therefor with -- or absence --.

Column 55,
Line 34, please delete "TNFa11b4cl d3e3", replace therefor with -- TNFa11b4cl d3e3 --.

Signed and Sealed this

Sixth Day of July, 2004

JON W. DUDAS
*Acting Director of the United States Patent and Trademark Office*